(12) United States Patent
Yum et al.

(10) Patent No.: US 8,956,644 B2
(45) Date of Patent: *Feb. 17, 2015

(54) TRANSDERMAL DELIVERY SYSTEMS

(71) Applicant: Durect Corporation, Cupertino, CA (US)

(72) Inventors: Su II Yum, Los Altos, CA (US); Sung Yun Kwon, Fremont, CA (US); Xiaoping Song, San Jose, CA (US); James E. Brown, Los Gatos, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,685

(22) Filed: Nov. 16, 2012

(65) Prior Publication Data

US 2013/0317456 A1    Nov. 28, 2013

Related U.S. Application Data

(63) Continuation of application No. 11/978,791, filed on Oct. 29, 2007, now Pat. No. 8,337,883.

(60) Provisional application No. 60/936,866, filed on Jun. 22, 2007, provisional application No. 60/856,656, filed on Nov. 3, 2006.

(51) Int. Cl.
*A61K 9/70* (2006.01)
*A61K 31/445* (2006.01)
*A61M 35/00* (2006.01)
*A61L 15/58* (2006.01)

(52) U.S. Cl.
CPC .............. *A61M 35/00* (2013.01); *A61K 9/7053* (2013.01); *A61K 31/445* (2013.01); *A61L 15/58* (2013.01); *A61K 9/7023* (2013.01)
USPC ........................... 424/448; 424/449; 514/315

(58) Field of Classification Search
CPC . A61K 31/445; A61K 9/7023; A61K 9/7053; A61K 15/58; A61M 35/00
USPC .................................................. 424/448, 449
See application file for complete search history.

(56) References Cited

U.S. PATENT DOCUMENTS

| | | | |
|---|---|---|---|
| 2,931,802 | A | 4/1960 | Toney |
| 3,743,398 | A | 7/1973 | Johnson et al. |
| 3,814,095 | A | 6/1974 | Lubens |
| 3,853,837 | A | 12/1974 | Fujino et al. |
| 3,992,365 | A | 11/1976 | Beddell et al. |

(Continued)

FOREIGN PATENT DOCUMENTS

| | | |
|---|---|---|
| AU | 8374575 | 8/1975 |
| CA | 2222567 | 12/1996 |

(Continued)

OTHER PUBLICATIONS

Blanco et al. "Transdermal application of bupivacaine-loaded poly (acrylamide(a)-co-monomethyl itaconate) hydrogels," Int. J. Pharmaceutics, vol. 255, No. 1-2, Jan. 14, 2003, pp. 99-107, XP002517808 ISSN: 0378-5173.

(Continued)

*Primary Examiner* — Rachael E Bredefeld

(57) ABSTRACT

Disclosed are bupivacaine transdermal delivery systems, and related methods.

32 Claims, 11 Drawing Sheets

(56) References Cited

U.S. PATENT DOCUMENTS

| | | |
|---|---|---|
| 4,024,248 A | 5/1977 | Konig et al. |
| 4,100,274 A | 7/1978 | Dutta et al. |
| 4,230,105 A | 10/1980 | Harwood |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,440,777 A | 4/1984 | Zupan |
| 4,487,603 A | 12/1984 | Harris |
| 4,530,840 A | 7/1985 | Tice et al. |
| 4,559,222 A | 12/1985 | Enscore et al. |
| 4,588,580 A | 5/1986 | Gale |
| 4,622,219 A | 11/1986 | Haynes |
| 4,692,147 A | 9/1987 | Duggan |
| 4,719,226 A | 1/1988 | Otsuka et al. |
| 4,725,442 A | 2/1988 | Haynes |
| 4,725,852 A | 2/1988 | Gamblin et al. |
| 4,765,974 A | 8/1988 | Tokuda et al. |
| 4,765,986 A | 8/1988 | Liedtke |
| 4,767,628 A | 8/1988 | Hutchinson |
| 4,795,641 A | 1/1989 | Kashdan |
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer |
| 4,906,474 A | 3/1990 | Langer |
| 4,938,759 A | 7/1990 | Enscore |
| 4,938,763 A | 7/1990 | Dunn et al. |
| 4,957,744 A | 9/1990 | Della Valle et al. |
| 4,970,075 A | 11/1990 | Oshlack |
| 4,990,341 A | 2/1991 | Goldie et al. |
| 5,069,909 A | 12/1991 | Sharma et al. |
| 5,070,084 A | 12/1991 | Campbell |
| 5,103,812 A | 4/1992 | Salamone et al. |
| 5,149,543 A | 9/1992 | Cohen |
| 5,188,837 A | 2/1993 | Domb |
| 5,234,957 A | 8/1993 | Mantelle |
| 5,266,331 A | 11/1993 | Oshlack et al. |
| 5,278,201 A | 1/1994 | Dunn et al. |
| 5,278,202 A | 1/1994 | Dunn et al. |
| 5,286,496 A | 2/1994 | Stapler et al. |
| 5,324,519 A | 6/1994 | Dunn et al. |
| 5,324,520 A | 6/1994 | Dunn et al. |
| 5,330,835 A | 7/1994 | Kikuchi et al. |
| 5,332,576 A | 7/1994 | Mantelle |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,635 A | 10/1994 | Raman et al. |
| 5,368,860 A | 11/1994 | Sunami et al. |
| 5,370,864 A | 12/1994 | Peterson et al. |
| 5,378,730 A | 1/1995 | Lee et al. |
| 5,382,424 A | 1/1995 | Stapler et al. |
| 5,391,381 A | 2/1995 | Wong et al. |
| 5,399,353 A | 3/1995 | Bartnik et al. |
| 5,399,363 A | 3/1995 | Liversidge et al. |
| 5,411,738 A | 5/1995 | Hind |
| 5,415,866 A | 5/1995 | Zook |
| 5,442,033 A | 8/1995 | Bezwada |
| 5,446,070 A | 8/1995 | Mantelle |
| 5,462,743 A | 10/1995 | Turner et al. |
| 5,474,783 A | 12/1995 | Miranda et al. |
| 5,478,577 A | 12/1995 | Sackler et al. |
| 5,487,898 A | 1/1996 | Lu et al. |
| 5,502,058 A | 3/1996 | Mayer et al. |
| 5,536,263 A | 7/1996 | Rolf et al. |
| 5,540,912 A | 7/1996 | Roorda et al. |
| 5,545,408 A | 8/1996 | Trigg et al. |
| 5,549,912 A | 8/1996 | Oshlack et al. |
| 5,563,153 A | 10/1996 | Meuller et al. |
| 5,569,450 A | 10/1996 | Duan et al. |
| 5,589,180 A | 12/1996 | Hind |
| 5,599,552 A | 2/1997 | Dunn et al. |
| 5,599,554 A | 2/1997 | Majeti |
| 5,599,852 A | 2/1997 | Scopelianos |
| 5,601,838 A | 2/1997 | Hind |
| 5,628,993 A | 5/1997 | Yamagata |
| 5,633,000 A | 5/1997 | Grossman et al. |
| 5,641,504 A | 6/1997 | Lee et al. |
| 5,656,295 A | 8/1997 | Oshlack et al. |
| 5,667,799 A | 9/1997 | Caldwell et al. |
| 5,672,360 A | 9/1997 | Sackler et al. |
| 5,702,716 A | 12/1997 | Dunn et al. |
| 5,709,869 A | 1/1998 | Hind |
| 5,719,197 A | 2/1998 | Kanios et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,741,510 A | 4/1998 | Rolf et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,776,952 A | 7/1998 | Liedtke |
| 5,777,124 A | 7/1998 | Zavareh et al. |
| 5,780,044 A | 7/1998 | Yewey et al. |
| 5,786,484 A | 7/1998 | Dyer et al. |
| 5,827,529 A | 10/1998 | Ono et al. |
| 5,840,329 A | 11/1998 | Bai |
| 5,866,157 A | 2/1999 | Higo et al. |
| 5,876,746 A | 3/1999 | Jona et al. |
| 5,879,705 A | 3/1999 | Heafield et al. |
| 5,885,597 A | 3/1999 | Botknecht et al. |
| 5,906,830 A | 5/1999 | Farinas |
| 5,919,473 A | 7/1999 | Elkhoury |
| 5,932,597 A | 8/1999 | Brown |
| 5,942,241 A | 8/1999 | Chasin et al. |
| 5,948,389 A | 9/1999 | Stein |
| 5,948,433 A | 9/1999 | Burton |
| 5,955,479 A | 9/1999 | Bardsley et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,096,334 A | 8/2000 | Rolf et al. |
| 6,103,771 A | 8/2000 | Galer et al. |
| 6,126,919 A | 10/2000 | Stefely et al. |
| 6,143,322 A | 11/2000 | Sackler et al. |
| 6,203,813 B1 | 3/2001 | Gooberman |
| 6,245,351 B1 | 6/2001 | Nara et al. |
| 6,291,013 B1 | 9/2001 | Gibson et al. |
| 6,299,902 B1 | 10/2001 | Jun et al. |
| 6,312,717 B1 | 11/2001 | Molinoff et al. |
| 6,348,210 B1 | 2/2002 | Gale |
| 6,375,978 B1 | 4/2002 | Kleiner et al. |
| 6,383,511 B1 | 5/2002 | Cassel |
| 6,384,227 B2 | 5/2002 | Dyer et al. |
| 6,403,609 B1 | 6/2002 | Asgharian |
| 6,413,536 B1 * | 7/2002 | Gibson et al. ............... 424/423 |
| 6,417,201 B1 | 7/2002 | Bardsley et al. |
| 6,420,454 B1 | 7/2002 | Wenz et al. |
| 6,426,339 B1 | 7/2002 | Berde et al. |
| 6,440,493 B1 | 8/2002 | Gibson et al. |
| 6,455,066 B1 | 9/2002 | Fischer et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,514,484 B2 | 2/2003 | Rajaiah et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,638,981 B2 | 10/2003 | Williams et al. |
| 6,645,521 B2 | 11/2003 | Cassel |
| 6,673,363 B2 | 1/2004 | Luo et al. |
| 6,699,908 B2 | 3/2004 | Sackler et al. |
| 6,733,783 B2 | 5/2004 | Oshlack et al. |
| 6,746,689 B2 | 6/2004 | Fischer et al. |
| 6,825,203 B2 | 11/2004 | Pasternak et al. |
| 6,921,541 B2 | 7/2005 | Chasin et al. |

(56) References Cited

U.S. PATENT DOCUMENTS

| | | |
|---|---|---|
| 6,992,065 B2 | 1/2006 | Okumu |
| 7,053,209 B1 | 5/2006 | Gibson et al. |
| 7,833,543 B2 | 11/2010 | Gibson et al. |
| 8,133,507 B2 | 3/2012 | Yum et al. |
| 8,153,149 B2 | 4/2012 | Verity |
| 8,153,661 B2 | 4/2012 | Verity |
| 2001/0000522 A1 | 4/2001 | Dyer et al. |
| 2001/0029257 A1 | 10/2001 | Murdock et al. |
| 2002/0001631 A1 | 1/2002 | Okumu |
| 2002/0009491 A1 | 1/2002 | Rothbard et al. |
| 2002/0114835 A1 | 8/2002 | Sackler et al. |
| 2002/0161018 A1 | 10/2002 | Smith et al. |
| 2003/0045454 A1 | 3/2003 | Okumu et al. |
| 2003/0082225 A1 | 5/2003 | Mason |
| 2003/0124174 A1 | 7/2003 | Galer |
| 2003/0152637 A1 | 8/2003 | Chasin et al. |
| 2003/0185873 A1 | 10/2003 | Chasin et al. |
| 2004/0001889 A1 | 1/2004 | Chen et al. |
| 2004/0024021 A1 | 2/2004 | Sudo et al. |
| 2004/0052336 A1 | 3/2004 | Langlet et al. |
| 2004/0068007 A1 | 4/2004 | Lee et al. |
| 2004/0076648 A1 | 4/2004 | Williams et al. |
| 2004/0086556 A1 | 5/2004 | Luo et al. |
| 2004/0101557 A1 | 5/2004 | Gibson et al. |
| 2004/0101582 A1 | 5/2004 | Wolicki et al. |
| 2004/0109893 A1 | 6/2004 | Chen et al. |
| 2004/0138237 A1 | 7/2004 | Shah |
| 2004/0146562 A1 | 7/2004 | Shah |
| 2004/0208914 A1 | 10/2004 | Richlin et al. |
| 2004/0224903 A1 | 11/2004 | Berry et al. |
| 2005/0042194 A1 | 2/2005 | Ng et al. |
| 2005/0106304 A1 | 5/2005 | Cook et al. |
| 2005/0171052 A1 | 8/2005 | Cook et al. |
| 2005/0209319 A1 | 9/2005 | Cundy et al. |
| 2005/0232876 A1 | 10/2005 | Minga et al. |
| 2005/0244489 A1 | 11/2005 | Paris |
| 2005/0266087 A1 | 12/2005 | Junnarkar et al. |
| 2006/0034926 A1 | 2/2006 | Fraatz et al. |
| 2006/0058401 A1 | 3/2006 | Ishikawa et al. |
| 2006/0165800 A1 | 7/2006 | Chen et al. |
| 2006/0210599 A1 | 9/2006 | Gibson et al. |
| 2007/0202156 A1 | 8/2007 | Seeki et al. |
| 2008/0023261 A1 | 1/2008 | Kaneko et al. |
| 2008/0145419 A1 | 6/2008 | Gibson et al. |
| 2008/0152708 A1 | 6/2008 | Gibson et al. |
| 2008/0206321 A1 | 8/2008 | Yum et al. |
| 2009/0023689 A1 | 1/2009 | Yum et al. |
| 2009/0023690 A1 | 1/2009 | Yum et al. |
| 2009/0037490 A1 | 2/2009 | Ohira |
| 2009/0130190 A1 | 5/2009 | Breitenbach et al. |
| 2011/0009451 A1 | 1/2011 | Verity |

FOREIGN PATENT DOCUMENTS

| | | |
|---|---|---|
| CA | 2283517 | 4/1998 |
| CA | 2291087 | 12/1998 |
| CA | 2303442 | 3/1999 |
| DE | 1569231 | 8/1969 |
| DE | 2213717 | 11/1972 |
| DE | 2321174 | 11/1973 |
| DE | 2438352 | 2/1976 |
| DE | 2720245 | 11/1977 |
| DE | 19520237 | 12/1996 |
| DE | 19714765 | 10/1998 |
| EP | 0244118 | 11/1987 |
| EP | 0290983 | 11/1988 |
| EP | 0331392 | 9/1989 |
| EP | 0413528 | 2/1991 |
| EP | 0535899 | 4/1993 |
| EP | 0539559 | 5/1993 |
| EP | 0156080 | 10/1993 |
| EP | 0635531 | 1/1995 |
| EP | 0488137 | 4/1995 |
| EP | 0671162 | 9/1995 |
| EP | 0525105 | 2/1996 |
| EP | 0711548 | 5/1996 |
| EP | 0640336 | 2/1997 |
| EP | 0507160 | 3/1997 |
| EP | 0773034 | 5/1997 |
| EP | 0537559 | 1/1998 |
| EP | 0539751 | 2/1998 |
| EP | 0621042 | 1/2000 |
| EP | 0999825 | 5/2000 |
| EP | 1010436 | 6/2000 |
| EP | 0758548 | 10/2000 |
| EP | 0754453 | 1/2002 |
| EP | 0782569 | 3/2002 |
| EP | 0804417 | 6/2003 |
| EP | 0788480 | 7/2003 |
| EP | 0788481 | 8/2003 |
| EP | 1348427 | 10/2003 |
| EP | 1032390 | 11/2003 |
| EP | 0778768 | 5/2004 |
| EP | 0674913 | 6/2004 |
| EP | 1063978 | 6/2004 |
| EP | 1548093 | 6/2005 |
| EP | 1212092 | 10/2005 |
| EP | 2238478 | 10/2010 |
| GB | 1088992 | 10/1967 |
| GB | 2163956 | 3/1986 |
| GB | 2238478 | 6/1991 |
| JP | 59210024 | 11/1984 |
| JP | 62000419 | 1/1987 |
| JP | 63302858 | 12/1988 |
| JP | 2096516 | 4/1990 |
| JP | 4501076 | 2/1992 |
| JP | 7053356 | 2/1995 |
| JP | 7070297 | 3/1995 |
| JP | 7112940 | 5/1995 |
| JP | 7115901 | 5/1995 |
| JP | 7124196 | 5/1995 |
| JP | 8505395 | 6/1996 |
| JP | 8206191 | 8/1996 |
| JP | 8512303 | 12/1996 |
| JP | 9502181 | 3/1997 |
| JP | 2000185091 | 7/2000 |
| JP | 5194273 | 4/2009 |
| JP | 4330175 | 6/2009 |
| WO | WO 903809 | 4/1990 |
| WO | WO 9003768 | 4/1990 |
| WO | WO 9117900 | 11/1991 |
| WO | WO 9118016 | 11/1991 |
| WO | WO 9217900 | 10/1992 |
| WO | WO 9303751 | 3/1993 |
| WO | WO 9307833 | 4/1993 |
| WO | WO 9405265 | 3/1994 |
| WO | WO 9415587 | 7/1994 |
| WO | WO 9501786 | 1/1995 |
| WO | WO 9506693 | 3/1995 |
| WO | WO 9509613 | 4/1995 |
| WO | WO 9517901 | 7/1995 |
| WO | WO 9609290 | 3/1996 |
| WO | WO 9612699 | 5/1996 |
| WO | WO 9612700 | 5/1996 |
| WO | WO 9622281 | 7/1996 |
| WO | WO 9639995 | 12/1996 |
| WO | WO 9641616 | 12/1996 |
| WO | WO 9715285 | 5/1997 |
| WO | WO 9727840 | 8/1997 |
| WO | WO 9749391 | 12/1997 |
| WO | WO 9824428 | 6/1998 |
| WO | WO 9827962 | 7/1998 |
| WO | WO 9827963 | 7/1998 |
| WO | WO 9834596 | 8/1998 |
| WO | WO 9844903 | 10/1998 |
| WO | WO 9851246 | 11/1998 |
| WO | WO 9853837 | 12/1998 |
| WO | WO 9906023 | 2/1999 |
| WO | WO 9913913 | 3/1999 |
| WO | WO 9925349 | 5/1999 |
| WO | WO 0000120 | 1/2000 |
| WO | WO 0078335 | 12/2000 |
| WO | WO 0115734 | 3/2001 |

(56) References Cited

FOREIGN PATENT DOCUMENTS

| | | |
|---|---|---|
| WO | WO 0151024 | 7/2001 |
| WO | WO 0176599 | 10/2001 |
| WO | WO 0210436 | 2/2002 |
| WO | WO 02053187 | 7/2002 |
| WO | WO 03000282 | 1/2003 |
| WO | WO 03041684 | 5/2003 |
| WO | WO 03086368 | 10/2003 |
| WO | WO 03101358 | 12/2003 |
| WO | WO 2004011032 | 2/2004 |
| WO | WO 2004037224 | 5/2004 |
| WO | WO 2004037289 | 5/2004 |
| WO | WO 2004052336 | 6/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005089872 | 9/2005 |
| WO | WO 2005105009 | 11/2005 |
| WO | WO 2005105031 | 11/2005 |
| WO | WO 2005115333 | 12/2005 |
| WO | WO 2006017632 | 2/2006 |
| WO | WO 2006033948 | 3/2006 |
| WO | WO 2006047362 | 5/2006 |
| WO | WO 2006084139 | 8/2006 |
| WO | WO 2006084141 | 8/2006 |
| WO | WO 2008023261 | 2/2008 |

OTHER PUBLICATIONS

Elsner (1995) *Current Problems in Dermatology: Irritant Dermatatis. New Clinical and Experimental Aspects* Ed. Maibach, vol. 23, p. 224-229, Basel, Karger.
European Search Report for European Application No. 12162550.3 dated Jul. 5, 2012, 8 pages.
Ferrar et al. (2001) "Clinical importance of changes in chronic pain intensity measured on an 11-point numerical pain rating scale" *Pain* 94(2):149-158.
Ghosh et al. (1997) "Design, Development, Manufacturing, and Testing of Transdermal Drug Delivery Systems" *Transdermal and Topical Drug Delivery Systems* Interferon Press, Ch. 8, p. 249-268.
Ghosh et al. (1997) "Safety Assessment of Transdermal and Topical Dermatological Products" *Transdermal and Topical Drug Delivery Systems* Interferon Press, Ch. 6, p. 191-214.
González et al. (2002) "Effects of Levobupivacaine, Ropivacaine and Bupivacaine on HERG Channels: Stereoselective Bupivacaine Block" *Br J Pharmacol* 137(8):1269-1279.
Kasting et al. (1987) "Effect of lipid solubility and molecular size on percutaneous absorption" *Pharmacol Skin* 1.
Kato et al. (2006) "Kinetic Analysis on the Skin Disposition of Cytotoxicity as an Index of Skin Irritation Produced by Cetylpyridinium Chloride: Comparison of In Vitro Data Using a Three-Dimensional Cultured Human Skin Model with In Vivo Results in Hairless Mice" *Pharm Res*.
Mize, et al. "Quantitative Structure-Activity Relationship and Cytotoxicity," Elsner P, Maibach HI, (eds.) Irritant Dermatitis, New Clinical and Experimental Aspects, Current Problems in Dermatology, Basel, Karger, Switzerland, 1995, vol. 23, pp. 224-229.
Sanchez et al. (2004) "Assessment of the Potential Skin Irritation of Lysine-Derivative Anionic Surfactants Using Mouse Fibroblasts and Human Keratocytes as an Alternative to Animal Testing" *Pharm Res* 21(9):1637-1641.
Turk et al. (1993) "Neglected Topics in Chronic Pain Treatment Outcome Studies: Determination of Sucess" *Pain* 53(1):3-16.
"3M DDS Announces Development of New HFA-Compatible Excipients: Novel Oligomeric Acids as MDI Suspension Aids and Solubilizers," 3M Delivery Newsletter, 3M Drug Delivery Systems, vol. 15, Jun. 2000.
"New Drugs/Programs", Current Drug Discovery, Nov. 2004 pp. 7-10.
"Polycaprolactone" http://en.wikipedia.org/wiki/polycaprolactone, 1 page, Jun. 16, 2008.
"Polyglycolide" http://en.wikipedia.org/wiki/polyglycolide, 3 pages, printed Jun. 16, 2008.
"Polylactic Acid" http://en.wikipedia.org/wiki/polylactic_acid, 1 page, printed Jun. 16, 2008.
Adams EG, et al. "A comparison of the abuse liability of tramadol, NSAIDS, and hydrocodone in patients with chronic pain." Journal of Pain and Symptom Management. 3 1(5), 465-476 2006.
Ahuja et al. (1995) "Intra-Articular Morphine Versus Bupivacaine for Postoperative Analgesia Following Knee Arthroscopy" *The Knee* 2(4):227-231.
Ajayaghosh, A., et al., "Solid-Phase Synthesis of N-Methyl and N-Ethylamides of Peptides Using Photolytically Detachable ((3-Nitro-4-((alkylamino)methyl) benzamido)methyl)polystrene Resin," J. Org. Chem., 55:2826 (1990).
Allahham A, et al. "Flow and injection characteristics of pharmaceutical parenteral formulations using a micro-capillary rheometer". Int J Pharm. 2004;270(1-2): 139-48.
Ansel, H.C. et al., Pharmaceutical Dosage Forms and Drug Delivery System, sixth ed., (1995).
Barb, R. et al., "Evaluation of the Saber Delivery System for the Controlled Release of Deslorelin: Effect of Dose in Estrogen Primed Ovarectomized Gilts," Proceed. Int'l Symp. Control. Rel. Bioact. Mater., 26 (1999).
Bartfield et al. (1998) "Randomized Trial of Diphenhydramine Versus Benzyl Alcohol with Epinephrine as an Alternative to Lidocaine Local Anesthesia" *Ann Emerg Med* 32(6):650-654.
Bartfield et al. (2001) "Benzyl Alcohol with Epinephrine as an Alternative to Lidocaine With Epinephrine" *J Emerg Med* 21(4):375-379.
Becker, S.E., et al. "Effects of Gonadotropin-Releasing Hormone Infused in a Pulsatile or Continuous Fashion on Serum Gonadotropin Concentrations and Ovulation in the Mare," J. Anim. Sci. (1992) 70:1208-1215.
Bekersky I, et al. "Effect of low- and high-fat meals on tacrolimus absorption following 5 mg single oral doses to healthy human subjects." J Clin Pharmacol 2001 ; 4 1 (2): 176-82.
Betschart, R., et al., "Evaluation of the Saber™. Delivery System for the Controlled Release of the GnRH Analogue Deslorelin for Advancing Ovulation in Mares: Effect of Gamma Radiation," Proceed. Int'l Symp. Control. Rel. Bioact. Mater. 25 (1998) Controlled Release Society, Inc. pp. 655-656.
Bhatia & Singh "Percutaneous Absorption of LHRH through Porcine Skin: Effect of N-Methyl 2 Pyrrolidone and Isopropyl Myristate" *Drug Development & Industrial Pharmacy* 23(11):1113-1114, (1997).
Brevard J, et al. "Pain and opioid abuse in a population of substance abuse patients: data from the NAVIPPRO system." Conference paper presented at the 42nd American Pain Society (APS) Annual Scientific Meeting, Washington D.C., 2007.
Buhler, K. GnRH Agonists and Safety, in GnRH Analogues the State of the Art 1993, a Summary of the 3rd International Symposium on GnRH Analogues in Cancer and Human Reproduction, Geneva, Feb. 1993.
Burns, P. et al., "Pharmacodynamic Evaluation of the Saber.TM. Delivery System for the Controlled Release of the GnRH Analogue Deslorelin Acetate for Advancing Ovulation in Cyclic Mares," Proceed. Int'l. Symp. Control. Rel. Bioact. Mater., 24 (1997), Controlled Release Society, Inc.
Cellulose Acetate Butyrate. In: European pharmacopoeia. 4 edn. Strasbourg Cedex, France: Council of Europe; 2001; p. 853-4.
Coy, et al., "Solid Phase Synthesis of Lutcinizing Hormone-Releasing Hormone and its Analogs," Methods Enzymol. 37, 416 (1975).
D 2857-95 (2001) "Standard Practice for Dilute Solution Viscosity of Polymers" Copyright by ASTM Int'l.
Desai, Neil P., et al. "Surface Modifications of Polymeric Biomaterials for Reduced Thrombogenicity," Polymeric Materials Science and Engineering, vol. 62, 1990 by ACS.
Dodson, K.M., et al. "Oral Controlled Release of Antiretrovirals Using the SABER Delivery System Incorporated into Soft Gelatin Capsules", AAPS Meeting, 1999, New Orleans, LA.

(56) References Cited

OTHER PUBLICATIONS

Duan, D. et al., "Novel Dispersing Aids for Hydrofluoroalkane-Based Metered Dose Inhalers," 1998 Conference of the American Association of Pharmaceutical Scientists, San Francisco, California, Nov. 1998.

Duan, D. et al., "Oligomeric Lactic Acids as Solubilizing Aids for HFA-Based Metered Dose Inhalers," 1998 Conference of the American Association of Pharmaceutical Scientists, San Francisco, California, Nov. 1998.

Dunbar SA, Katz NP "Chronic opioid therapy for nonmalignant pain in patients with a history of substance abuse: report of 20 cases." Journal of Pain and Symptom Management. 1 1 (3), 163-1 7 1. 1996.

English Translation of Japanese Office Action dated Mar. 6, 2012 for Japanses Patent Application No. 2009-108881.

English Translation of Japanese Office Action dated Mar. 6, 2012 for Japanses Patent Application No. 2009-2735.

Fitzgerald, B.P, et al., (1993) "Effect of Constant Administration of a Gonadotropin-Releasing Hormone Agonist on Reproductive Activity in Mares: Preliminary Evidence on Suppression of Ovulation During the Breeding Season," Am. J. Vet. Res., 54(10):1746-1751.

Fleury, J., et al., "Evaluation of the Saber.TM. Delivery System for the Controlled Release of the Deslorelin for Advancing Ovulation in the Mare: Effects of Formulation & Dose," Proceed. Int'l. Symp. Control. Rel. Bioact. Mater. 25 (1998) Controlled Release Society, Inc. pp. 657-658.

Gilderman L., et al. "Remoxy™: A New Opioid Drug With Effective Analgesia and Abuse-Resistance." American Pain Society Annual Meeting, San Antonio, TX, May 2006.

Ginther, O.J. et al. "Effect of a Synthetic Gonadotropin-Releasing Hormone on Plasma Concentrations of Luteinizing Hormone in Ponies," Am. J. Vet. Res., 35: 79-81 (1974).

Ginther, O.J., "Ultrasonic Imaging and Reproductive Events in the Mare," Equiservices, Cross Plains, WI Chapter 4:43-72 (1986).

Ginther, O.J., Reproductive Biology of the Mare: Basic and Applied Aspects, EquiServices, Chapter 12, 499-508 Cross Plains, Wisconsin (1970).

Glajchen, M. "Chronic Pain: Treatment Barriers and Strategies for Clinical Practice." J Am Board Fam Pract. 2001 ; 14(3): 178-183.

Harrison, L., et al. "Comparison of HCG, Buserelin and Luprostiol for Induction of Ovulation in Cyclling Mares," J. Eq. Vet. Sci., 11:163-166 (1991).

Hatakeyama, et al. "Synthesis and Physical Properties of Polyurethanes from Saccharide-Based Polycaprolactones" *Macromolecular Symposia* 130(1):127-138, (1998).

Hays LR. "A profile of OxyContin addiction. Journal of Addictive Diseases." 23 (4), 1-9. 2004.

Henry, C. (1995) "Sucrose Acetate Isobutyrate Special Grade for Beverage Applications" *International Food Ingred.* pp. 47-49.

Hoskin PJ, et al. "The bioavailability and pharmacokinetics of morphine after intravenous, oral and buccal administration in healthy volunteers." Br J Clin Pharmacol 1989; 27 (4):499-505.

Hyland, J.H., et al. "Infusion of Gonadotrophin-Releasing Hormone (GnRH) Induces of Ovulation and Fertile Oestrus in Mares During Seasonal Anoestrus," J. Reprod. Fert., Suppl. 35 (1987), 211-220.

Inciardi et al. (2007) "Mechanisms of prescription drug diversion among drug-involved club-and street-based populations" Pain Medicine. 8(2), 17 1-183.

Irvine, C.H.G., "GnRH Clinical Application," in Equine Reproduction, (eds) McKinon, A.O. and Voss, J.L., Chapter 36, pp. 41-45, Lea & Febiger (1993).

Irvine, D.S., "Duration of Oestrus and Time of Ovulation in Mares Treated with Synthetic GnRH (Ay24,031)," J. Reprod. Fert. Supp. 23:279-283 (1975).

Ishida T, Oguri K, et al. "Isolation and identitication of urinary metabolites of oxycodone in rabbits." Drug Metab Dispos 1979; 7 (3): 162-5.

Ishida T, Oguri K, Yoshimura H. "Determination of oxycodone metabolites in urines and feces of several mammalian species." J Pharmacobiodyn 1982; 5 (7):52 1-5.

Iyakuhin Tenkabutsu Kenkyykai Ed. "Jitsuyo Iyakuhin Tenkabutsu (Practical Medical Additives)" pub. Kagaku Kogyo-sha Mar. 5, 1974, Tokyo.

Japanese Office Action for Japanese Patent Application No. 2007-532447 mailed Nov. 15, 2011.

Jochle, W., et al., Control of Ovulation in the Mare with Ovuplant. TM., a Short-Term Release Implant (STI) Containing the GNRH Analogue Deslorelin Acetate: J. Eq. Vet. Sci., 44:632 (1994).

Johnson & Verity (2002) "Applications of Continuous Site-Directed Drug Delivery" *Proc West Pharmacol Soc* 45:219-222.

Johnston LD, O'Malley PM, Bachman JG, Schulenberg, JE. "Monitoring the future. National results on adolescent drug use: overview of key findings" (NIH Publication No. 05-5726). Bethesda, MD: National Institute on Drug Abuse 2004.

Katz NP, et al. "Behavioral monitoring and urine toxicology testing in patients receiving long-term opioid therapy." Anesth Analg. 97(4), 1097-102. (2003).

Katz NP, et al. "Challenges in the development of prescription opioid abuse-deterrent formulations." Clin J Pain. 2007;23(8):648-60.

Katz NP, et al. "Development and preliminary experience with an ease of extractability rating system for prescription opioids." Drug Development and Industrial Pharmacy. 32(6) 727-746(20). 2006.

Katz NP, et al. "Prescription monitoring of medical and non-medical Schedule I/ opioid abuse in Massachusetts: 1996-2005." Conference paper presented at the 69th College on Problems of Drug Dependence (CPDD), Quebec, Canada, 2007.

Kulkarni et al., "Polyactic Acid for Surgical Implants," Arch. Surg., 93:389 (1966).

Lacoste, D., et al., "Reversible Inhibition of Testicular Androgen Secretion by 3-, 5-and 6-Month Controlled -Release Microsphere Formulations of teh LH-RH Agonist [D-Trp.sup.6, des-Gly-NH.sub. 2.sup.10 ] LH-RH Ethylamide in the Dog," J. Steroid Biochem. 33:5, 1007-1011 (1989).

Lalovic B, et al. "Pharmacokinetics and pharmacodynamics of oral oxycodone in healthy human subjects: role of circulating active metabolites" Clin Pharmacol Ther 2006; 79 (5):461-79.

Loy, R.G. et al. "The Effects of Human Chorionic Gonadotrophin on Ovulation, Length of Estrus, and Fertility in the Mare," Cornell Vet. 56:41-50 (1966).

Material Safety Data Sheet of Eastman Chemical Products, "SAIB" Sucrose Acetate Isobutyrate, Publication GN-311F (Jun. 2004).

Material Safety Data Sheet of Eastman Chemical Products, "SAIB" Sucrose Acetate Isobutyrate, pp. 2-18. (2004).

Material Safety Data Sheet of Eastman Fine Chemical Pharmaceutical Ingredients, Sucrose Acetate Isobutyrate Special Grade (SAIB-SG), Publication No. EFC-211, (May 1991).

Material Safety Data Sheet of Eastman Products for the Food Industry, "Sucrose Acetate Isbutyrate (SAIB-SB) for Use in Fruit-Flavored Beverages," Publication No. ZM-90, pp. 2-7 (Sep. 1989).

Mather & Chang (2001) "Cardiotoxicity with Modern Local Anaesthetics: Is There a Safer Choice?" *Drugs* 61(3):333-342.

McCabe et al. "Motives, diversion and routes of administration associated with nonmedical use of prescription opioids." Addictive Behaviors. 32, 562-575. 2007.

McCarthy, P. et al., "Management of Stallions on Large Breeding Farms," Stallion Management, vol. 8, No. 1, Apr. 1992, pp. 219-235.

McKinnon, A.O., et al. "Effect of a GnRH Analogue (Ovuplant), hCG and Dexamethasone on Time to Ovulation in Cycling Mares." World Equine Veterinary Review, (1997) 2:3 16-18.

McKinnon, A.O., et al. "Repeated Use of a GnRH Analogue Deslorelin (Ovuplant) for Hastening Ovulation in the Transitional Mare," Equine Vet. J., (1996) 29:2 153-155.

McLellan AT, Luborsky L, Woody GE, O'Brien CP. "An improved 'diagnostic instrument for substance abuse patients." The Addiction Severity Index. J Nerv Ment Dis. 1980; 168:26-33.

Mearns, "Changing Seasons," The Blood-Horse, Sep. 28, 1996, p. 4794-4795.

Merrifield, B., "Solid Phase Synthesis" Science 232:342 (1986).

Meyer RJ, et al. Awareness topic: mitigating the risk of ethanol induced dose dumping from oral sustained controlled release dosage forms. In: FDA's Advisory Committee for Pharmaceutical Science Meeting, Oct. 2005.

(56) References Cited

OTHER PUBLICATIONS

Montovan, S.M., et al., "The Effect of a Potent GnRH Agonist on Gonadal and Sexual Activity in the Horse," Theriogenology, 33:6, 1305-1321 (1990).

Mumford, E.L. et al., "Use of Deslorelin Short-Term Implants to Induce Ovulation in Cycling Mares During Three Consecutive Estrov Cycles," Animal Reproduction Science, 139 (1995) 129-140.

Murray S, et al. "Alcohol-associated rapid release of a long-acting opioid" CMAJ 2005; 173(7):756.

Nakagaki, Arita, "Seizai Butsuri Kagaku (Physical Chemistry of Medical Preparations)", pub. Asakura Shoten, Nov. 5, 1968, Tokyo.

Nally, J., et al., "Induction of Mucosal IgA Specific for SeMF3 for *Streptococcus* equi with Intranasal Vaccination Using a Sucrose Acetate Isobutyrate Based Delivery System", Proceed. Int'l. Symp. Control. Rel. Bioact. Mater., 26 (1999) Controlled Release Society, Inc.

Nett et al., "Further Studies on the Radioimmunoassay of Gonadotropin-Releasing Hormone: Effect of Radioiodination, Antiserum and Unextracted Serum on Levels of Immunoreactivity in Serum," Endocrinology 101:1135 (1977).

Pulido et al., "Enzymatic Regioselective Acylation of Hexoses and Pentoses Using Oxime Esters.", J. Chem. Soc. Perkin Trans. 1, (21), 2891-2898, 1992.

Rabb et al., "Effects of Active Immunication Against GnRH on LH, FSH and Prolactin Storage, Sectretion and Response to Their Secretagogues in Pony Geldings," J. Anim Sci., 68:3322-3329.

Reynolds, R.C. et al., "Sucrose acetate isobutyrate (SAIB): historical aspects of its use in beverages and a review of toxicity studies prior to 1988," Food Chem. Toxicol., 1998,36 (2), pp. 81-93.

Reynolds, R.C., "Metabolism and pharmacokinetics of sucrose acetate isobutyrate (SAIB) and sucrose octaisobutyrate (SOIB) in rats, dogs, monkeys or humans: a review," Food Chem. Toxicol., 1998,36 (2), pp. 95-99.

Roser, J.J., et al., "The Development of Antibodies to Human Chorionic Gonadotrpins Following its Repeated Injection in the Cyclic Mare," J. Reprod. Fert. Suppl., 173-179 (1979).

Sullivan, J., "Duration of Estrus and Ovulation Time in Nonlactating Mares Given Human Chorionic Gonadotropin During Three Successive Estrous Periods," J. Am. Vet. Med. Assoc., 63:895 (1973).

Sullivan, S. A., 1998, "Sustained Release of Orally Administered Active Using Saber™ Delivery System Incorporated into Soft Gelatin Capsules" Proceed. Int'l Symp. Control. Rel. Bioact. Mater.., 25:918-919.

Swiderski, et al. "Application of 14CIsotope in Studies of Liability of Sugar Substituents" Nukleonike, Supl. 10:347-352. (1996).

Thompson, Jr., D.L., et al., "Effects of Melatonin and Thyrotropin Releasing Hormone of Mares Durign the Nonbreeding Season," J. Anim. Sci., 58:3, 668-677(1983).

Thompson, Jr., D.L., et al., "Testosterone Effects on Mares During Synchronization with Altrenogest: FSH, LH, Estrous, Duration and Pregnancy Rate," J. Anim. Sci., 56:3, 678-686 (1983).

Trescot AM, et al. "Opioid Guidelines in the Management of Chronic Non-Cancer Pain." Pain Physician. 2006;9: 1-40.

University of Utah, Department of Chemical Engineering (2006) "A Viscosity Primer: Viscosity Definitions" http://www.che.utah.edu/department_eguipment/Projects_Lab/A_Viscometers/ViscosityDefinitions.pdf.

Vega-Rios A, Villalobos H, Mata-Segreda JF. "Acid-catalyzed hydrolysis of triacylglycerols obeys monoexponential kinetics." Int J Chem Kinet. 1992; 24:887-94.

Voss, J.L. et al. "The Effect of HCG on Duration of Oestrus, Ovulation Time and Fertility in Mares," J. Reprod. Fert., Suppl. 23 (1975) 297-301.

Wilson et al. (1999) "Benzyl Alcohol as an Alternative Local Anesthetic" *Ann Emerg Med* 33(5):495-499.

Gammaitoni, Arnold R. et al, (2003) "Safety and Tolerability of the Lidocaine Patch 5%, a Targeted Peripheral Analgesic: A Review of the Literature", J Clin Pharmacol, 43:111-117.

Higgins, J. J. et al., (1989) "Butyl Rubber and Polyisobutylene", Handbook of Pressure Sensitive Adhesive Technology, Satas & Associates, Warwick, Rhode Island, 321-345.

(2009) "Indopol Polybutene" Product Bulletin, INEOS Oligomers, League City, TX, 36 pages.

(2013) "Eastman SAIB and Eastman Sustane SAIB (sucrose acetate isobutyrate)" Product Bulletin, Eastman Chemical, Kingsport, TN, 12 pages.

(2004) "Eastman(TM) SAIB-100, Industrial Grade", Material Safety Data Sheet, Eastman Chemical, Kingsport, TN, 1 page.

\* cited by examiner

TRANSDERMAL DELIVERY SYSTEMS

This application claims priority to 60/936,866 and 60/856,656, both of which applications are hereby incorporated by reference in their entirety.

FIELD OF THE INVENTION

The invention relates generally to transdermal delivery systems and related methods. More particularly the invention relates to transdermal delivery systems and related methods for transdermally delivering bupivacaine through the skin.

BACKGROUND OF THE INVENTION

Local pain disorders comprise pain that is specific to a particular tissue or region of a subject. For instance, certain types of neuropathic pain, such as post-herpetic neuralgia, are local pain disorders. Likewise, certain other types of pain, such as low back pain, are local pain disorders.

Many medications are used for the treatment of pain, ranging from well known, over-the-counter compounds such as aspirin, acetaminophen, ibuprofen and other non-steroidal anti-inflammatory compounds to newer chemical entities such as the cyclooxygenase II inhibitor compounds or narcotics such as opioids. Many such analgesics are used systemically, in order to treat non-localized pain.

What is needed is a transdermal delivery system that addresses the problems in the art associated with treatment of local pain disorders, together with related methods.

SUMMARY OF THE INVENTION

In an aspect, the invention relates to a method comprising: applying to a subject a transdermal delivery system that comprises bupivacaine; transdermally delivering the bupivacaine from the transdermal delivery system for a period to the subject such that the following mean plasma concentrations are achieved: a mean plasma concentration, normalized to an initial loading of the transdermal delivery system, ranging from about 0.0003 to about 0.7 $cm^2/L$ at about 12 hours after initiation of the transdermal delivery; and a mean plasma concentration, normalized to an initial loading of the transdermal delivery system, ranging from about 0.0014 to about 0.4 $cm^2/L$ at about 24 hours after initiation of the transdermal delivery.

In another aspect, the invention relates to a transdermal delivery system comprising: a backing layer, and a reservoir laminated to the backing layer that comprises bupivacaine; and wherein the reservoir is adapted to transdermally deliver the bupivacaine from the transdermal delivery system to a subject for a period such that the following mean plasma concentrations are achieved: a mean plasma concentration, normalized to an initial loading of the transdermal delivery system, ranging from about 0.0003 to about 0.7 $cm^2/L$ at about 12 hours after initiation of the transdermal delivery; and a mean plasma concentration, normalized to an initial loading of the transdermal delivery system, ranging from about 0.0014 to about 0.4 $cm^2/L$ at about 24 hours after initiation of the transdermal delivery.

In a further aspect, the invention relates to a method comprising: applying to a subject a transdermal delivery system that comprises bupivacaine; transdermally delivering the bupivacaine from the transdermal delivery system to the subject for a three day period at one or more transdermal delivery rates such that the following relationships, normalized to an initial loading of the transdermal delivery system, are satisfied during the three day period:

$$0.003 \leq Cmax \leq 0.76 \, cm^2/L, \text{ and } 0.124 \leq AUC \leq 11.2 \, cm^2 \cdot hr/L.$$

In an aspect, the invention relates to a transdermal delivery system comprising: a backing layer, and a reservoir laminated to the backing layer that comprises bupivacaine; and wherein the reservoir is adapted to transdermally deliver the bupivacaine from the transdermal delivery system to a subject for a three day period such that the following relationships are satisfied during the three day period: $0.003 \leq Cmax \leq 0.76 \, cm^2/L$, and $0.124 \leq AUC \leq 11.2 \, cm^2 \cdot hr/L$.

In still another aspect, the invention relates to a method comprising: applying to a subject a transdermal delivery system that comprises bupivacaine; transdermally delivering the bupivacaine from the transdermal delivery system to the subject for a period such that the following mean in vivo bupivacaine fluxes are achieved: a mean in vivo bupivacaine flux from about 0.1 to about 8 microgram/$cm^2$/hr at about 12 hours after initiation of the transdermal delivery; and a mean in vivo bupivacaine flux from about 0.5 to about 6 microgram/$cm^2$/hr at about 24 hours after initiation of the transdermal delivery.

In yet another aspect, the invention relates to a method comprising: applying to a subject a transdermal delivery system that comprises bupivacaine; transdermally delivering the bupivacaine from the transdermal delivery system to the subject such that the mean in vivo bupivacaine fluxes at any time from about 12 hours after initiation of the transdermal delivery to about 48 hours after initiation of the transdermal delivery range from about 0.01 to about 25 microgram/$cm^2$/hr.

In a further aspect, the invention relates to a method comprising: applying to a subject a transdermal delivery system that comprises bupivacaine; transdermally delivering the bupivacaine from the transdermal delivery system to the subject such that the mean in vivo bupivacaine fluxes at any time from about 12 hours after initiation of the transdermal delivery to about 72 hours after initiation of the transdermal delivery range from about 0.01 to about 25 microgram/$cm^2$/hr.

In an aspect, the invention relates to a transdermal delivery system comprising: a backing layer, and a reservoir laminated to the backing layer that comprises bupivacaine; and wherein the reservoir is adapted to transdermally deliver the bupivacaine from the transdermal delivery system to a subject for a three day period such that the following mean in vivo bupivacaine fluxes are achieved: a mean in vivo bupivacaine flux from about 0.1 to about 8 microgram/$cm^2$/hr at about 12 hours after initiation of the transdermal delivery; and a mean in vivo bupivacaine flux from about 0.5 to about 6 microgram/$cm^2$/hr at about 24 hours after initiation of the transdermal delivery.

In still another aspect, the invention relates to a method comprising: applying to a transdermal delivery system that comprises bupivacaine; transdermally delivering the bupivacaine from the transdermal delivery system such that the following mean in vitro bupivacaine fluxes are achieved: a mean in vitro bupivacaine flux ranging from about 0.1 to about 8 microgram/$cm^2$/hr at about 12 hours after initiation of the transdermal delivery; and a mean in vitro bupivacaine flux ranging from about 0.25 to about 6 microgram/$cm^2$/hr at about 24 hours after initiation of the transdermal delivery.

In an aspect, the invention relates to a method comprising: applying a transdermal delivery system that comprises bupivacaine; transdermally delivering the bupivacaine from the transdermal delivery system such that a mean in vitro bupivacaine flux at any time from about 12 hours after initiation of the transdermal delivery to about 48 hours after initiation of the transdermal delivery ranges from about 0.01 to about 25 microgram/cm$^2$/hr.

In yet another aspect, the invention relates to a method comprising: applying a transdermal delivery system that comprises bupivacaine; transdermally delivering the bupivacaine from the transdermal delivery system such that a mean in vitro bupivacaine flux at any time from about 12 hours after initiation of the transdermal delivery to about 72 hours after initiation of the transdermal delivery ranges from about 0.01 to about 25 microgram/cm$^2$/hr.

In an aspect, the invention relates to a transdermal delivery system comprising: a backing layer, and a reservoir laminated to the backing layer that comprises bupivacaine; and wherein the reservoir is adapted to transdermally deliver the bupivacaine from the transdermal delivery system to a subject for a three day period such that the following mean in vitro bupivacaine fluxes are achieved: a mean in vitro bupivacaine flux from about 0.1 to about 8 microgram/cm$^2$/hr at about 12 hours after initiation of the transdermal delivery; and a mean in vitro bupivacaine flux from about 0.5 to about 6 microgram/cm$^2$/hr at about 24 hours after initiation of the transdermal delivery.

In another aspect, the invention relates to a transdermal delivery system comprising: a backing layer, and a reservoir comprising a pressure sensitive adhesive composition laminated to the backing layer; wherein the pressure sensitive adhesive composition comprises one or more rheology and surface energy modifying agents present in an amount effective to reduce a peel force of the transdermal delivery system by at least 10% compared to the peel force of the transdermal delivery system comprising the pressure sensitive adhesive composition that does not comprise the one or more rheology and surface energy modifying agents.

In an aspect, the invention relates to a transdermal delivery system comprising: a backing layer, and a reservoir comprising a pressure sensitive adhesive composition laminated to the backing layer; wherein the pressure sensitive adhesive composition comprises from about 10 to about 30 wt. % of a polyisobutyrate having a viscosity average molecular weight of about 1,100,000, from about 5 to about 40 wt. % of a polyisobutyrate having a viscosity average molecular weight of about 50,000, from about 30 to about 70 wt. % of polybutene, from about 0.1 to about 10 wt. % of sucrose acetate isobutyrate, and from about 1 to about 10 wt. % of bupivacaine, where the weight % is based on the total weight of the pressure sensitive adhesive composition in a dry state.

In a further aspect, the invention relates to a transdermal delivery system comprising:

a backing layer, and a reservoir laminated to the backing layer that comprises bupivacaine; wherein the reservoir is adapted to transdermally deliver the bupivacaine from the transdermal delivery system to a subject for a three day period; and wherein the transdermal delivery system is sterile.

In an aspect, the invention relates to a method comprising: applying to a transdermal delivery system that comprises bupivacaine; transdermally delivering the bupivacaine from the transdermal delivery system for a two day period, wherein a residual amount of bupivacaine in the transdermal delivery system following the two day period of use ranges from about 20 wt % to about 85 wt %, based on the total weight of bupivacaine in the transdermal delivery system prior to transdermal delivery.

In yet another aspect, the invention relates to a method comprising: applying to a transdermal delivery system that comprises bupivacaine; transdermally delivering the bupivacaine from the transdermal delivery system for a three day period, wherein a residual amount of bupivacaine in the transdermal delivery system following the two day period of use ranges from about 20 wt % to about 85 wt %, based on the total weight of bupivacaine in the transdermal delivery system prior to transdermal delivery.

These and other objects, aspects and advantages of the present invention will readily occur to the skilled practitioner upon reading the instant disclosure and specification.

DETAILED DESCRIPTION OF THE INVENTION

Figure 1:
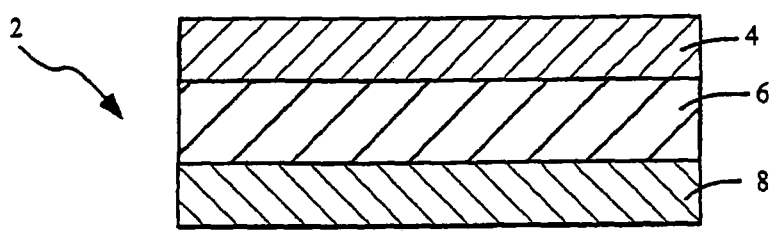
FIG. 1 shows a cross-sectional view through a transdermal delivery system according to the present invention.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

As used in this specification and the appended claims, the singular forms "a," "an" and "the" include plural referents unless the content clearly dictates otherwise. For example, reference to "a polymer" includes a mixture of two or more such molecules, reference to "a solvent" includes a mixture of two or more such compositions, reference to "an adhesive" includes mixtures of two or more such materials, and the like.

A. Introduction

The inventors have unexpectedly realized that it may be possible to provide efficacious bupivacaine treatments for local pain by providing the inventive TDSs and related methods.

Many systemic analgesics create systemic side effects. For instance, systemic opioids can generate constipation, and may become addictive in certain subjects. Therefore, in certain circumstances, analgesics that are locally acting may be employed. One class of locally acting analgesics comprises local anesthetics. Local anesthetics are hypothesized to act mainly by inhibiting sodium influx through sodium-specific ion channels in the neuronal cell membrane, in particular the so-called voltage-gated sodium channels. When the influx of sodium is interrupted, an action potential cannot arise and signal conduction is believed to be inhibited. There are several members of the class of local anesthetics, including bupivacaine.

Bupivacaine is a locally acting anesthetic agent, therefore systemic plasma concentrations do not signify the activity of the drug. They are, however, indicative of the side effects. These include generalized convulsions, coma, respiratory arrest, bradycardia, and tachyarrhythmia. Ultimately, such side effects may lead to death. Bupivacaine's toxicity, especially its CNS toxicity and its cardiotoxicity, is a concern when bupivacaine is administered conventionally (e.g. parenterally), using conventional routes of administration and conventional dosages.

Additionally, bupivacaine may be conventionally disfavored as a choice of local anesthetic particularly for chronic administration. This is because of its potential for skin irritation. Skin irritation is a major drawback for the successful development of TDSs. T. K. Ghosh et al., "Transdermal and Topical Drug Delivery Systems", Chapter 6, Interpharm Press (1997). A correlation has been suggested between the Log P of a compound and its potential for skin irritation. In N. Mize et al., "Quantitative Structure-Activity Relationship and Cytotoxicity," Curr. Problems in Dermatology 23:224-229 (1995) ("Mize et al."), a correlation was developed from testing of 92 compounds of widely varying therapeutic class and chemical structure. This correlation was expressed as Equation 1 below:

$$\text{Log } 1/IC50 = 0.43(+/-0.06)\log P + 1.71(+/-0.19) \quad (1)$$

$$R=0.85, SD=0.46, n=92$$

In Equation 1, P is the octanol/water partition coefficient, and IC50 is a value obtained that represents viability of human dermal fibroblasts in the presence of the drug being tested, using the MTT assay. Id. The MIT assay is widely known as a measurement of skin irritation dermatodynamics. See generally L. Sanchez et al., "Assessment of the Potential Skin Irritation of Lysine-Derivative Anionic Surfactants Using Mouse Fibroblasts and Human Keratocytes as An Alternative to Animal Testing," Pharm. Res. 21(9): 1637-1641 (2004); and S. Kato et al., "Kinetic Analysis on the Skin Disposition of Cytotoxicity as an Index of Skin Irritation Produced by Cetylpyridinium Chloride: Comparison of In Vitro Data using a Three-Dimensional Cultured Human Skin Model with In Vivo Results in Hairless Mice," Pharm. Res. 23(2):329-335 (2006).

Equation 1 reflects a positive correlation between an increase in Log P and an increase in skin irritation caused by a compound. Therefore, when selecting a compound for transdermal delivery, it would be desirable to select a compound that had a low log P, so as to decrease at least one source of skin irritation caused by that compound. In this regard, bupivacaine would be a disfavored choice because it has a log P of around 3.4, as compared for instance with other local anesthetics such as lidocaine (log P of around 2.4), mepivacaine (log P of around 1.95), or ropivacaine (log P of around 2.9).

To the best of the Applicants' knowledge, bupivacaine has never been successfully delivered locally to a human subject using a transdermal delivery system until the present invention. Accordingly, until the present invention bupivacaine has not been actually characterized in terms of its transdermal flux through human skin. It remained doubtful whether bupivacaine would have sufficient transdermal flux to make a successful bupivacaine transdermal delivery system. Its transdermal flux through rabbit ear skin has been reported. M. D. Blanco et al., "Transdermal application of bupivacaine-loaded poly(acryalamide(A)-co-monomethyl itaconate) hydrogels", Int J Pharm 14:255(1-2):99-107 (2003). However, rabbit ear skin flux is not a good predictor of performance with human skin.

Further, at least one model that is predictive of drug flux through human skin suggests that bupivacaine has a lower or equivalent human skin flux as compared to other local anesthetics. In Kasting et al., Pharmacol. Skin 1 (1987) ("Kasting"), a set of constant flux contours for percutaneous absorption of drugs through human epidermis (in vitro at 30° C.) is presented. Using the molecular weight and melting point for several local anesthetics in free base form, the following results are obtained, with maximum flux expressed in units of micrograms/cm² hours:

TABLE 1

Predicted Skin Fluxes for Various Local Anesthetics

| Compound | Molecular Weight | Melting Point | Predicted Flux(max) |
| --- | --- | --- | --- |
| Lidocaine | 234.34 | 68° C. | 99 |
| Bupivacaine | 288.43 | 107° C. | 12 |
| Mepivacaine | 247.81 | 150° C. | 8 |
| Ropivacaine | 274.00 | 145° C. | 8 |

As can be seen, bupivacaine has a much lower predicted human skin flux than lidocaine, and about the same predicted human skin flux as mepivacaine or ropivacaine. These results, when compared against one another, suggest a clear human skin flux disadvantage to selecting bupivacaine to make a TDS useful in the treatment of local pain disorders. Accordingly, use of this model tends to teach away from selecting bupivacaine to provide an bupivacaine transdermal delivery system effective for local analgesia, in favor of a local anesthetic with a higher flux like lidocaine.

As noted above, efficacious bupivacaine TDSs have not been known in the art. Prior to the present invention, it was not known in the art what fluxes might be expected from an applied bupivacaine TDS to a subject. Additionally, prior to the present invention it was not known whether any flux from a bupivacaine TDS into a subject could reach sufficient local tissue concentrations to be supportive of efficacy of the TDS. Indeed, predictive skin flux models tended to suggest that it might not be possible for a bupivacaine TDS to provide efficacious local tissue concentrations.

The data presented herein suggests, surprisingly, that the inventive bupivacaine TDS can transdermally deliver substantial amounts of bupivacaine to a subject. Example 11 sets out the systemic pharmacokinetic data associated with use of the inventive TDSs. The plasma concentration, in vitro and in vivo flux, and Cmax & AUC values claimed reflect the delivery rates of bupivacaine to the patient, and therefore represent the advantages of the present invention. The system plasma concentration curves associated with the present invention can be seen in FIGS. 6 and 7. Bupivacaine flux values, both in vitro and in vivo, can be seen in FIG. 4. Furthermore, results from human clinical trials suggest that the amount of bupivacaine transdermally delivered by the inventive TDSs may be sufficient to provide effective local analgesia.

Figure 9:
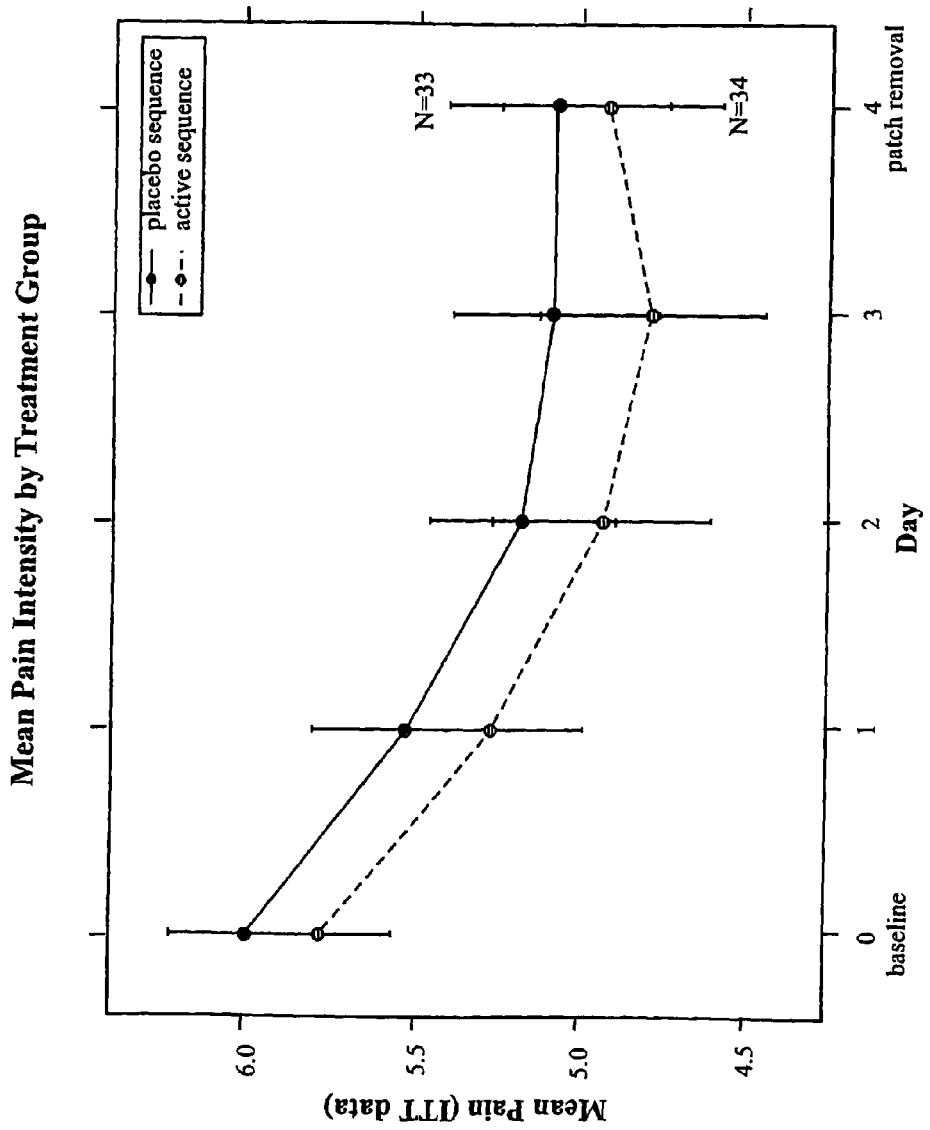
FIG. 9 shows a plot of Mean Pain Intensity by Treatment Group.

Data in Example 13, which sets forth the results from an interim analysis of a placebo-controlled human clinical trial, support the hypothesis that the inventive TDSs generate sufficient bupivacaine skin flux so as to provide a level of pain relief. Mean daily pain intensity, as measured using an 11-point Numeric Rating Scale (PI-NRS), was analyzed in accordance with the pre-specified analysis method (at the study level, irrespective of period, and by treatment sequence). As shown in FIG. 9, the results show a beneficial trend in favor of subjects on the active arm having lower pain PI-NRS scores than subjects on placebo. This is echoed by results from assessments of subject global impression of change (SGIC), which are provided in FIG. 12. These data suggest a trend that subjects on the active arm had a one point better global impression than patients on placebo. Likewise, the proportion of subjects achieving at least a 20% improvement (relative to baseline) in terms of mean daily pain intensity is shown in Table 13 below. The difference between the proportion of subjects achieving at least a 20% improvement was 51.5% for placebo and 62.9% for active. However, an investigation into the amount of rescue medication used by subjects was inconclusive.

The claimed Cmax & AUC ranges are significant because they reflect a range of plasma concentrations not previously appreciated in the art: those plasma concentrations that are efficacious but not cardiotoxic. Plasma concentrations of bupivacaine previously known in the art are those associated with parenteral administration. Such plasma concentrations may have concerning levels of cardiotoxicity, especially with respect to other possible local anesthetics known in the art. One straightforward way to reduce cardiotoxicity would be to select another, potentially less cardiotoxic local anesthetic. Instead, the inventors decided to reduce the amount of drug administered, thus reducing systemic concentration, in order to see if this resulted in acceptable cardiotoxicity levels. Until the invention by the applicants, it was unknown and unpredictable whether this approach would significantly reduce bupivacaine systemic concentration but still retain local efficacy. The ranges claimed by applicants are believed to accomplish just that, based in part on the data presented herein, which is supportive of their criticality and non-obviousness.

The plasma concentration, in vitro and in vivo flux, and the Cmax & AUC values claimed also reflect the duration of application of the inventive TDSs, which has clinical advantages in and of itself, such as increased protection of the locus of pain and less skin irritation associated with application/removal cycles.

The inventive TDSs provide relatively non-irritating systems that can be left in place on or around loci of pain for periods of at least preferably one day, more preferably two days, and still more preferably at least three days. This is an important advantage because use of a transdermal delivery system, as compared to a cream or ointment-type delivery vehicle, helps to protect the locus of pain and reduces the level of hyperallodynia associated with undesirable stimulation of the sensitized pain locus of pain. Additionally, repeated application and removal cycles can irritate the locus of pain and create additional pain for the subject. Every time that a transdermal delivery system of any type is removed from the skin of a subject some of the surface skin cells are removed. Therefore, reducing the repetition of application and removal cycles by increasing the duration of action can help to reduce irritation, thus increasing comfort and possibly subject compliance. Support for this can be seen in Example 11, which presents the results of a skin irritation study using TDS embodiments according to the present invention.

Example 11 addresses the unexpected results of the present invention with respect to skin irritation. With its relatively high Log P of 3.4, bupivacaine would have been expected by one of skill in the art, in light of Mize et al., to be more irritating to a subject's skin than other choices of local anesthetics such as lidocaine. Applicants tested this conventional wisdom, and found that contrary to expectations, the inventive TDS bupivacaine displayed an acceptable level of skin irritation. In fact, only 1 out of 6 subjects (16.7%) displayed mild erythema when the TDS was left on the subject's skin for 3 days (Part 2). This compares with Part 1 of the study, in which application and removal of the TDS on a daily basis resulted in mild erythema that was observed in 8 out of 8 (100%) subjects. Applicants have shown that frequent applications and removals of TDSs is far more irritating to the skin than continuous 3 day transdermal delivery of bupivacaine. Additionally, the data presented in Example 13, which was obtained as part of the interim analysis of a human clinical trial, suggest that the level of skin and subcutaneous tissue disorders is actually about 3 times higher for patients in the placebo arm as compared to patients in the active arm. Accordingly, the results from Example 11 and Example 13 are in agreement. These results were unexpected in light of the teachings of Mize et al., as discussed above, which taught away from choosing a relatively high Log P compound, such as bupivacaine, for transdermal administration.

The inventors have also addressed skin irritation concerns by developing embodiments of the inventive transdermal delivery systems with controllable peel force. As seen in Example 12, addition of RSEMAs can reduce peel force (conversely, removal of RSEMAs can increase peel force), and therefore enable tailoring of the transdermal delivery system's characteristics to suit a particular use. As the level of the selected RSEMA in Example 12, which is sucrose acetate isobutyrate, goes from 0 wt % to 5 wt %, the peel force at a given strain rate decreases. This is particularly noticeable at the strain rate ranges likely to be encountered when a subject is removing the transdermal delivery system from their skin. Reductions in peel force may be advantageous in treatment of local pain disorders, because lower peel forces may reduce trauma to a subject's skin associated with application and removal cycles. Reduction in trauma to that area of a subject's skin can increase the comfort (and thus the subject's compliance) associated with repeated application of the inventive transdermal delivery systems, because the inventive transdermal delivery systems are preferably applied on or near the locus of pain.

The inventive transdermal delivery systems possess patentable compositions as well. The compositions of the inventive TDSs are of interest because they provide for effective transdermal delivery for periods of at least days and, in preferable embodiments, can do so without requiring permeation enhancers or additional excipients that could be irritating to the skin site. Additionally, the inventive compositions provide for a reduction in peel force, as discussed above. Examples 1-8 show several embodiments of the present invention having different recipes for the reservoir, in the form of a pressure sensitive adhesive. Example 9 describes in vitro flux testing of embodiments of the present invention and Example 10 describes dissolution testing of embodiments of the present invention.

The invention will now be discussed in more detail.

B. Definitions

"Area under the curve" or "AUC" means the total area under the plasma bupivacaine concentration curve. It is calculated from the time of administration to the time point of the last measurable plasma drug concentration using a trapezoidal method plus an extrapolation to infinity according to the ratio of the last measurable plasma drug concentration to the apparent slope of the terminal (natural) log linear portion of the plasma drug concentration profile.

"Bupivacaine" means 1-butyl-N-(2,6-dimethylphenyl)-2-piperidinecarboxamide. In certain embodiments, bupivacaine according to the invention comprises the racemic form of the compound. In certain embodiments, bupivacaine according to the invention comprises the levo enantiomer of the compound, which may be referred to as levobupivacaine. The form of bupivacaine that is preferred to be used in the practice of this invention comprises bupivacaine free base, also known as bupivacaine base, although lipophilic permeable pharmaceutically acceptable salts may be used in the practice of this invention. The molecular weight of bupivacaine base is 288.43. Bupivacaine is relatively fast acting, and maintains analgesia for periods longer than many other local anesthetics.

"Bupivacaine flux" or "transdermal flux" means the amount of bupivacaine transported across a surface, such as a subject's skin, per unit of surface area. In an embodiment, the flux is determined in vivo, meaning that the flux is determined for a subject or group of subjects. In another embodiment, the flux is determined in vitro, meaning that the flux is determined using test equipment such as a Franz cell with cadaver skin, or equivalent in vitro test methods.

"Cmax" means a mean systemic plasma maximum concentration of a substance, determined within a specific interval and without interpolation.

"Initial loading" means the amount of bupivacaine per unit area of the inventive TDS immediately prior to initiating transdermal delivery of the bupivacaine. Various metrics may be normalized to this amount, including but not limited to plasma concentrations.

"Mean plasma concentration" means the average plasma concentration taken across subjects, when there are multiple subjects, or at different times with adequate washout periods, when there is a single subject.

"Pressure sensitive adhesive composition" and "pressure sensitive adhesive" mean a material that displays adherence when pressed together with the surface of another material.

"Residual amount" means the amount of bupivacaine remaining in a TDS following its use. As the inventive TDSs are intended to be repositionable, the period of use may vary. In an embodiment, the residual amount is determined after the TDS has been in use for two days. In another embodiment, the residual amount is determined after the TDS has been in use for three days.

"Sterile" means a degree of sterility in accordance with the applicable standards set forth by the Association for the Advancement of Medical Instrumentation (AAMI).

"Subject" is used interchangeably with "individual" and means any human with which it is desired to practice the present invention. The term "subject" does not denote a particular age, and the present systems are thus suited for use with subjects of any age, such as infant, adolescent, adult and senior aged subjects In certain embodiments, a subject may comprise a patient.

"Three days" means a period of approximately 72 hours. It includes three "daytimes" and three "nighttimes."

"Transdermal delivery" or "transdermally delivering" means delivery or delivering of bupivacaine across the tissues of the skin.

"Transdermal delivery rates" means the rate of delivery of bupivacaine across the tissues of the skin.

"Transdermal delivery system" or "TDS" means a pharmaceutical dosage form that comprises either a liquid, gel or a matrix reservoir device. Both of these configurations may include a backing layer that provides a protective outer surface for the devices, as well as a release liner or layer that covers the adhesive portion of the device that is used to affix the same to the skin of a subject. The release liner is removed prior to application, thereby exposing the adhesive portion of the device, which will typically be a pressure-sensitive adhesive.

"Two days" means a period of approximately 48 hours. It includes two "daytimes" and two "nighttimes."

C. Transdermal Delivery Systems

In certain preferred embodiments, the inventive transdermal delivery systems comprise bupivacaine. Bupivacaine as a local anesthetic has certain advantages over other local anesthetics, including relatively fast onset of action and relatively long-lasting analgesic effect. Bupivacaine also possesses the necessary physical properties, such as but not limited to, molecular weight, charge density, log P, and melting point, for its successful inclusion in a transdermal delivery system.

Figure 2:
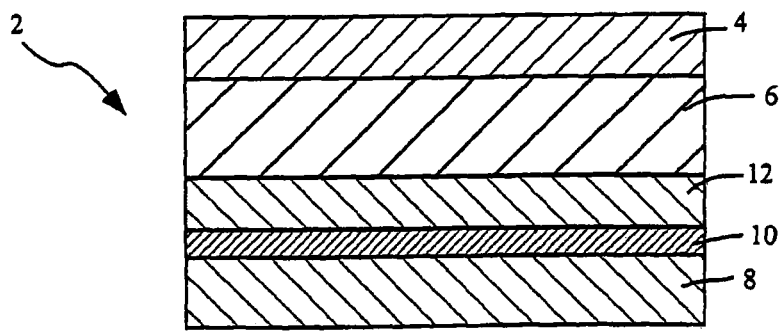
FIG. 2 shows a cross-sectional view through another transdermal delivery system according to the present invention.

The transdermal delivery systems of the invention may be provided as either a liquid or gel reservoir-type or a matrix-type device. Both of these configurations will naturally include a backing layer that provides a protective outer surface for the devices, as well as a release liner or layer that will cover the adhesive portion of the device that is used to affix the same to the skin of a subject. The release liner is removed prior to application, thereby exposing the adhesive portion of the device, which will typically be a pressure-sensitive adhesive. Accordingly, referring to FIGS. 1 and 2, a transdermal delivery system is generally indicated at 2. The device includes a backing layer 4, a reservoir 6 that contains bupivacaine, and a release liner 8. The reservoir 6 may be a liquid or gel reservoir, or it may be a matrix carrier that can be self-adhesive or non-adhesive. Referring specifically to FIG. 2, in those devices where the reservoir is either a liquid or gel reservoir, or a non-adhesive matrix, the device 2 will further comprise an adhesive layer 10 that serves to adhere the device to the skin. The adhesive layer 10 is generally a drug-permeable, drug-compatible, and inert adhesive that is applied over the reservoir. In some devices, a further layer 12 can be employed as a rate controlling membrane, where the layer is selected to provide for selective movement of bupivacaine through the layer.

In one particular embodiment, the inventive adhesive transdermal delivery systems are provided as a dimensionally stratified family of transdermal patches of varying doses, all having an adhesive matrix with a drug releasing interface surface area of from about 70 to about 140 cm$^2$. The superior adhesive and reapplicability properties displayed by the inventive transdermal delivery systems further allow for in-clinic size reduction procedures, where a particular patch can be divided into halves, thirds or quarters, to provide a different, fully operable patch having a reduced size and therefore a reduced size of treatment area. In this regard, indicia may be provided on the backing of the subject patches to facilitate accurate division of a particular patch into two or more patches of smaller size and dose. Cuttability of the present transdermal delivery systems is desirable for treating local pain areas of different sizes, configurations, curvatures and movement.

The backing layer 4, which adheres to the drug-containing reservoir 6 serves as the upper layer of the device during use and functions as the primary structural element of the device.

The backing layer is thus typically a sheet or film of a preferably flexible elastomeric material. This backing layer 4 typically has a thickness of about 0.1 to 50 mils, preferably about 0.5 to 30 mils, and more preferably about 1 to 25 mils, and is generally a material that permits the device to follow the contours of the skin such that it can be worn comfortably on any skin area including joints or other areas of flexure.

Accordingly, there is a reduced likelihood of the device dislodging from the skin due to differences in the flexibility or resiliency of the skin and the device, as well as in response to normal mechanical strain brought about by movement and the like. The backing layer may further be a monolithic (single layer) or a multi-layer (multilaminate), and may further be a breathable or occlusive material comprising woven or non-woven fabric. Most commonly, the backing layer 4 will be a polymeric material, or a laminate of polymeric materials. Suitable materials include, but are not limited to, polyethylene, polypropylene, polyesters, polyurethanes, polyethylene vinyl acetate, polyvinylidene chloride, block copolymers such as PEBAX, polyvinyl acetate, polyvinylidene chloride, polyurethane, ethylene vinyl acetate, polyethylene terephthalate, polybutylene terephthalate, coated paper products, metal or metalized sheets and the like, and any combinations thereof.

In preferred embodiments, the backing layer 4 comprises a non-woven polyester fabric. In a particularly preferred embodiment, the backing layer is a non-woven polyester fabric (e.g. DuPont's Sontara™ or Softesse™ fabric, Style 8005). Such non-woven polyester fabrics exhibit improved breathability and may be less irritating to skin without substantially reducing skin flux.

The reservoir 6 is disposed on the backing layer. The reservoir may be formed from any number of standard materials well known in the art. In those devices where the reservoir is a liquid or gel-type reservoir, any suitable gelling agent may be used to form an aqueous gel system, for example cellulose materials. In those devices where the reservoir is a matrix-type reservoir, it may be formed from any polymeric material in which bupivacaine has some solubility within a desired solubility range, for example, a polyurethane, ethylene/vinyl acetate copolymer (EVA), polyacrylate, styrenic block copolymer, and the like. It is preferred that the reservoir 6 is en adhesive type matrix, formed from a pharmaceutically acceptable pressure sensitive adhesive, preferably a polyisobutylene, polyacrylate or a styrenic block copolymer-based adhesive.

More particularly, in those embodiments of the invention where the transdermal delivery system is provided as a monolithic, adhesive matrix device, the reservoir 6 can be formed from standard pressure sensitive adhesives known in the art. Suitable pressure sensitive adhesives for use in the practice of the invention thus include, but are not limited to, polyacrylates, polysiloxanes, polyisobutylene (PIB), polyisoprene, polybutadiene, styrenic block polymers, blends and combinations of the above, and the like. Suitable styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof. Suitable acrylic polymers are comprised of a copolymer or terpolymer comprising at least two or more exemplary components selected from acrylic acids, alkyl acrylates, methacrylates, copolymerizable secondary monomers or monomers with functional groups. Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. See, e.g., Satas (1989) "Acrylic Adhesives," *Handbook of Pressure-Sensitive Adhesive Technology*, 2nd ed., pp. 396-456 (D. Satas, ed.), Van Nostrand Reinhold, N.Y. In a preferred embodiment, the pressure-sensitive adhesive is an acrylate having no functional groups or cross linkers (e.g., DURO-TAK® 87-9301, available from National Starch & Chemical, Bridgewater, N.J.), or a blend of acrylate-vinylacetates having —COOH and —OH functional groups (DURO-TAK® 87-2051 and 87-2287, National Starch & Chemical).

In certain other preferred embodiments, the reservoir 6 is formed from a monolithic adhesive matrix containing a polyisobutylene material. The polyisobutylene preferably comprises a blend of a high molecular weight polyisobutylene (about 450,000 to 2,100,000 viscosity average molecular weight) and a low molecular weight polyisobutylene (about 1,000 to 450,000 viscosity average molecular weight). In the polyisobutylene compositions of the present invention it is preferred that the high molecular weight: low molecular weight polyisobutylene in these compositions are used in a ratio of from about 20:80 to about 70:30, preferably between about 40:60 to about 50:50.

In a particularly preferred embodiment, the pressure-sensitive adhesive is a combination of low and high molecular weight polyisobutylene (PIB) polymers, for example, a high molecular weight PIB having a viscosity average molecular weight of about 1,100,000 (OPPANOL® B100, available from BASF, North Mount Olive, N.J.) and a low molecular weight PIB having a viscosity average molecular weight of about 50,000 (OPPANOL® B 12 SFN, available from BASF). In another preferred embodiment, the pressure-sensitive adhesive is a combination of a high molecular weight PIB having a viscosity average molecular weight of about 1,100,000 (VISTANEX® MM L-100, available from Exxon-Mobil, Houston, Tex.) and a low molecular weight PIB having a viscosity average molecular weight of about 50,000-55,000 (OPPANOL® B 11 SFN, available from BASF). As plasticizer or tackifier, either mineral oil or polybutene is added into the PIB based pressure sensitive adhesive. Light mineral oil as specified in the United States Pharmacopia or the Indopol® brand of polybutene (e.g. Indopol® H100) preferably can function as the plasticizer. The preferred range of the plasticizer concentration is from 10-70 wt. % of the total weight of the pressure sensitive adhesive composition ("PSA").

In practice, the material forming the reservoir 6 has a solubility for the bupivacaine of about 1 wt % to about 25 wt % of the total PSA material; preferably about 1 wt % to about 20 wt %; more preferably about 2 wt % to about 15 wt %; and even more preferably about 2 wt % to about 10 wt %. The reservoir 6, with or without the adhesive coating 3, has a thickness ranging from about 1 to about 10 mils.

The reservoir 6 further includes bupivacaine and may also contain optional ingredients, such as carriers, vehicles, additives, excipients, stabilizers, dyes, diluents, plasticizers, tackifying agents, crystallization inhibitors, solubility enhancers, inert fillers, antioxidants, anti-irritants, vasoconstrictors and other materials without pharmacological activity that are suitable for administration in conjunction with the transdermal delivery systems of the present invention. These optional materials are pharmaceutically acceptable in that they are nontoxic, do not interfere with delivery of bupivacaine from the system, and are not for any other reasons biologically or otherwise undesirable. If a pressure sensitive adhesive is used in accordance with the present invention, this must also be pharmaceutically acceptable. Examples of illustrative materials include water, mineral oil, silicone, inorganic gels, aqueous emulsions, liquid sugars, waxes, petroleum jelly, and a variety of other oils and polymeric materials.

In preferred embodiments, the PSA excludes or substantially excludes permeation enhancers. However, in other embodiments of the present invention where increased drug delivery rate per unit area of patch or skin bupivacaine flux is required, various skin permeation enhancing methods can be incorporated into the present invention. For example, one or more of chemical permeation enhancers can be added into the drug reservoir or thermal energy can be applied to the skin surfaces under the present invention patch or the present invention patch can be applied on the skin sites which is pretreated mechanically or chemically.

In certain transdermal delivery systems of the invention where the reservoir is an adhesive matrix, the reservoir 6 comprises one or more materials capable of improving its adhesive characteristics such as by reducing quick tack (tackifying agents), reducing cold-flow, increasing viscosity, and/or toughening the matrix structure. Examples of suitable materials include, but are not limited to, aliphatic hydrocarbons; aromatic hydrocarbons; hydrogenated esters; polyterpenes; polybutenes, silicone dioxide, silica, hydrogenated wood resins; tackifying resins, aliphatic hydrocarbon resins made from cationic polymerization of petrochemical feedstocks or the thermal polymerization and subsequent hydrogenation of petrochemical feedstocks, rosin ester tackifiers, mineral oil, polybutylmethacrylate, high molecular weight acrylates, and any combinations thereof.

In certain systems, the reservoir 6 comprises one or more rheology and surface energy modifying agents ("RSEMA") that improve the adhesive properties of the device, for example by promoting skin friendly removal and reapplication of the present transdermal delivery systems. RSEMA may further serve to reduce the abuse potential of the transdermal delivery system by preferentially associating with bupivacaine to provide a composition that resists extraction of bupivacaine under typical abuse conditions (alcohol extraction). The material can be a high viscosity liquid carrier material ("HVLCM") that is non-water soluble, and has a viscosity of at least 5,000 cP, (and optionally at least 10,000, 15,000; 20,000; 25,000 or even 50,000 cP) at 37° C. and that does not crystallize neat under ambient or physiological conditions. A particularly preferred RSEMA is sucrose acetate isobutyrate (SAIB) or some other ester of a sugar alcohol moiety with one or more alkanoic acid moieties. Additional RSEMAs comprise 1,6-hexanediol lactate glycolate, 1,6-hexanediol lactate caproate, glycerol lactate caproate, glycerol lactate glycolate, glycerol lactate glycolate with succinic anhydride, glycolic acid lactate glycolate, lactic acid lactate glycolate, and other materials with bioadhesion modifying qualities.

In practice, a small amount of the RSEMA is added to a pressure-sensitive material such as a PIB or acrylic adhesive base. Due to the low hydrophobicity and low surface tension of the RSEMA, this enables the resultant adhesive-RSEMA mixture to retain pressure sensitive properties even after the system has been applied and removed from the skin surface a number of times. This in turn allows the subject wearing a long-duration patch to remove the device during showering or heavy exercise, and then reapply the device without losing adhesion. When a transdermal patch is removed from skin, a certain number of dead skin cells (e.g. stratum corneum) are removed from the skin, with the result that the PSA loses adhesiveness. However, the transdermal delivery systems of the present invention preferably contain RSEMA at concentrations ranging from 0.01-25 wt. %, more preferably from about 1 to about 10 wt % RSEMA. Such embodiments remove the dead cells at a much lower number per unit area compared to PSAs without RSEMA. These concentrations of RSEMA reduce the skin peel forces and hence the amount of dead skin cells the PSA removes. This occurs to the extent that the surfaces of PSAs containing RSEMA remains patent or bioadhesive even after a number of removal-reapplication cycles.

U.S. Pat. No. 6,348,210 to Gale ("Gale") describes transdermal delivery systems that can be applied and then removed. However, the transdermal delivery systems of Gale have not been available for clinical use, suggesting an unmet need despite the teachings of Gale. Therefore, the repositionability/reapplicability of the inventive transdermal delivery systems represents progress in the art. The reduced peel force of the inventive transdermal delivery systems, as discussed further elsewhere herein, further aids in repositionability/reapplicability because removing an inventive transdermal delivery system is less painful and easier to accomplish as compared to a conventional transdermal delivery system. Therefore, a subject is more likely to be willing to move an inventive transdermal delivery system so as to optimized its location relative to the locus of pain.

In those systems where a plasticizer is utilized, the reservoir can further comprise a plasticizer material that is typically an inert, organic, apolar, nonvolatile hydrophobic liquid. In particular, the plasticizer may be a hydrophobic liquid. Suitable plasticizer materials thus include, but are not limited to, various long-chain aliphatic esters and alcohols, including such materials as polybutene, mineral oil, linseed oil, octyl palmitate, squalene, squalane, silicone oil, isobutyl stearate, olive oil, isopropyl myristate, isostearyl alcohol, oleyl alcohol, and the like.

Particularly preferred for use herein is polybutene, for example IDOPOL® L-14 or H-100 (available from BP Amoco, Naperville, Ill.), having a viscosity substantially equivalent to light mineral oil.

In addition, the reservoir can include one or more filler materials. Suitable fillers include, but are not limited to, metal oxides, inorganic salts, synthetic polymers, clays and the like. The metal oxides may be silicon dioxide, zinc oxide, magnesium oxide, titanium oxide, and calcium oxide. Inorganic salts can be calcium, magnesium and sodium carbonate, calcium and magnesium sulfate, calcium phosphate, and the like. Synthetic polymers can include methacrylic resin, nylon, polyethylene, and the like. Suitable clay compounds include talc, bentonite and kaolin.

Referring again to FIGS. 1 and 2, the device 2 further comprises a peelable release liner 8. The release liner is a disposable element that serves only to protect the device prior to application to the skin. Typically, the release liner is formed from a material impermeable to bupivacaine and other components of the system, and easily removable from the reservoir. Suitable materials comprise various polymeric materials that may be optionally metallized. Examples of suitable polymeric materials comprise polyurethane, polyvinyl acetate, polyvinylidene chloride, polypropylene, polycarbonate, polystyrene, polyethylene, polyethylene terephthalate, polybutylene terephthalate, polymer coated papers and combinations thereof. In preferred embodiments, the protective layer comprises a siliconized sheet (e.g. Medirelease paper silicone or PE from Mylan Tech, St. Albans, Vt.), or has a fluoropolymer coating (e.g. SCOTCHPAK® 9744 (available from 3M, St. Paul, Minn.).

Referring now to FIG. 2, certain transdermal delivery systems of the invention may include an adhesive layer 10 that serves to adhere the device 2 to the skin. The adhesive layer 10 is generally a drug-permeable pressure sensitive adhesive that is applied over the reservoir. Standard pressure sensitive adhesives are well known in the art. Suitable pressure sensitive adhesives for use in the adhesive layer 10 thus include, but are not limited to, polyacrylates, polysiloxanes, polyisobutylenes (PIB), polyisoprenes, polybutadienes, styrenic block polymers, blends and combinations of the above, and the like. These materials are disclosed in greater detail elsewhere herein. The adhesive layer may also serve the purpose of a rate controlling layer or membrane. However, in some systems, a further layer 12 is added as a rate controlling membrane. Suitable rate controlling membrane materials are known in the art and include, but are not limited to, low to high density polyethylene, ethylene vinyl acetate, polyurethane, and styrene poly-butadiene. Although a number of different transdermal delivery system configurations are suitable for use in practicing the current invention, it is preferred that the systems are provided as a monolithic device, where the bupivacaine is contained in an adhesive matrix adhered to a backing layer.

In embodiments, bupivacaine can be present in the system in an amount of about 1-20 weight percent (wt %) relative to the total system, preferably in an amount of about 1-20 wt %, preferably in an amount of about 1-12 wt %. In a preferred embodiment, an inventive TDS comprises about 0.1 to about 0.5 mg/cm$^2$ bupivacaine, more preferably about 0.293 mg/cm$^2$ bupivacaine. A preferred composition of the transdermal delivery systems of the present invention comprises: Oppanol B100 from about 10 to about 30 wt. %, Oppanol B12 SFN from about 5 to about 40 wt. %, Indopol H100 from about 30 to about 70 wt. %, SAIB from about 0.1 to about 10 wt. % and bupivacaine base from about 1 to about 10 wt. %, where the weight % is based on the total weight of the dried PSA composition. A more preferred composition of the transdermal delivery systems of the present invention comprises: Oppanol B100 from about 15 to about 20 wt. %, Oppanol B12 SFN from about 15 to about 25 wt. %, Indopol H100 from about 45 to about 65 wt. %, SAIB from about 1 to about 7 wt. %, and bupivacaine base from about 2 to about 7 wt. %, where the weight % is based on the total weight of the dried PSA composition.

All of the transdermal delivery systems of the present invention can be readily manufactured using known techniques. For example, to produce matrix-type systems, a solution of a suitable polymeric reservoir material can be added to a double planetary mixer, followed by addition of desired amounts of bupivacaine. Typically, the polymeric reservoir material is an adhesive polymer, which can be solubilized in an organic solvent, e.g., ethanol, ethyl acetate, and hexane. After mixing has taken place for a suitable period of time to achieve acceptable uniformity of the ingredients, the resultant mixture can be feed into a casting die. In such cases, the matrix/bupivacaine mixture is cast as a wet film onto a release liner carried on a moving web or belt, which is drawn through lines. A series of ovens is then used to evaporate the casting solvent to acceptable residual limits. A selected backing membrane can then be laminated onto the dried reservoir film. In subsequent operations, individual transdermal patches are die-cut, separated and unit-packaged. In other processes, a reservoir can be formed using dry-blending and thermal film-forming using equipment known in the art. Preferably, the materials are dry blended and extruded using a slot die followed by calendering to an appropriate thickness.

When manufacturing certain preferred monolithic systems according to the invention that include a polyisobutylene/polyisobutylene blend as the matrix, it is preferable to use low molecular weight hydrocarbon solvents like heptane, hexane, or cyclohexane. Preferably, the mixture of polyisobutylene compositions includes from about 60 to 85% by weight of the solvent, more preferably from about 65 to about 80% by weight of the solvent.

A preferred manufacturing process for a monolithic bupivacaine transdermal delivery system prepared according to the invention is as follows. Pre-weighed amounts of both high and low molecular weight PIBs and polybutene are added into glass vessels containing pre-measured amount of n-heptane and the containers are sealed. The PIB fractions and polybutene in the sealed containers are completely dissolved in n-heptane at room temperature by the actions of a rotating mixer. Mixing of the n-heptane polymer solution may continue in case when one or more of the inactive ingredients needs to be added in the polybutene-PIB formulations. Selective additives in small quantities can be added at the expense of all other non-solvent materials in the solution.

A pre-weighed amount of bupivacaine base is added to the above n-heptane solutions of polybutene-polyisobutylene and the bupivacaine solution is generated following mixing of bupivacaine base and the vehicle, using magnetic stirring equipment or an over head mixer at room temperature. Then, stirring action is stopped for approximately 15 minutes, air bubbles are removed from the bupivacaine solution, which is now ready to be transferred on a piece of release liner for precision-thickness coating using either a motorized film applicator (Elcometer, Inc.) or square multiple clearance applicators (Gardner PG&T Co.).

The wet bupivacaine solution films on the release liner section are air-dried for approximately 20 minutes at room temperature and 30 minutes at 70° C. in a convection oven (Blue M Electric, CSP Series Class A Oven). The oven dried bupivacaine films coated on the release liner are cooled to room temperature and a precut piece of the backing layer is laminated onto the reservoir/release liner using an aluminum roller (diameter: 1 in., length: 6 in.) or a modified motorized film applicator (Elcometer, Inc.) to squeeze and eliminate air pockets out of the reservoir/release liner laminates.

The final steps of the bupivacaine transdermal delivery system fabrication include die cutting the final laminates, using steel rule dies (Apex Die, Inc.) and a punch press (Schmidt Toggle Press, Schmidt Feintechnik Corp.) into the required system size. Appearance of the cut edges of the systems is examined. The total thickness and weight of the systems are determined using a pair of calipers (Mitutoyo Corp.) and a precision balance, respectively and recorded.

The systems are then placed into pouches (Barex® lined or Surlyn® lined or Bare-aluminum foil lined or Polypropylene lined pouch material, all of which are non-absorbing surfaces for bupivacaine base from the bupivacaine transdermal delivery systems), and the open ends of the pouches are heat sealed using an impulse heat sealer (Impulse Heat Sealer, Clamco). The pouches are labeled appropriately and counted and recorded.

Figure 3:
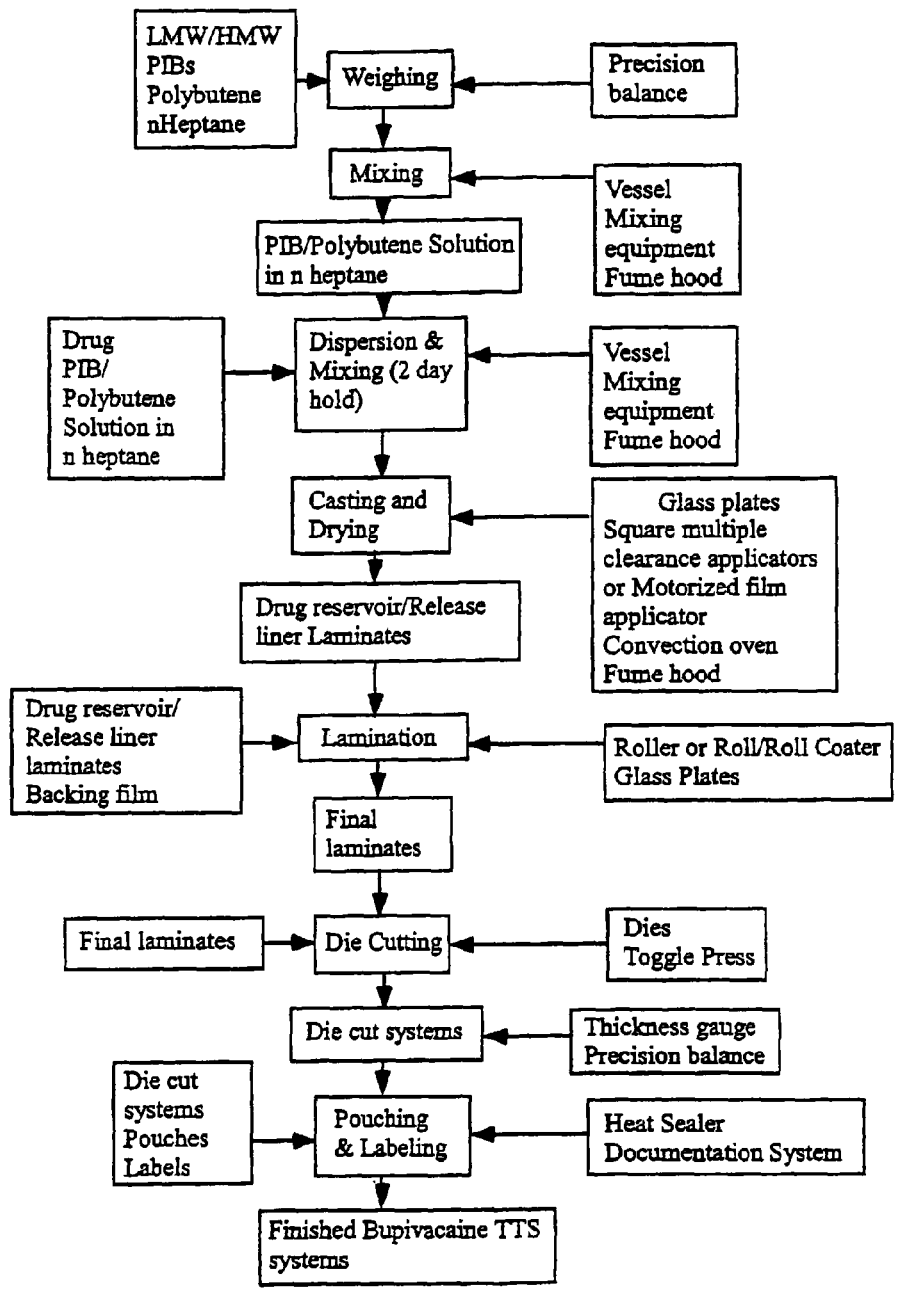
FIG. 3 shows a schematic representation of a manufacturing process for producing a transdermal delivery system according to the present invention.

Referring now to FIG. 3, a flow diagram illustrating the system manufacturing steps, along with materials, tools and equipment that are required for each unit operation for the systems is provided.

D. Administration

The inventive transdermal delivery systems are intended to relieve pain for a prolonged period of time, preferably for at least two days, and more preferably for at least three days.

In embodiments, inventive systems provide a net flux of bupivacaine from the system through the skin of about 0.01 µg/cm$^2$/hour to about 15 µg/cm$^2$/hour. In certain other embodiments, flux-max/flux-min for the first two day period ranges from about 0.1 to about 10 ug/cm$^2$ hr, and flux-max/flux-min for the first three day period ranges from about 0.1 to about 10 ug/cm$^2$ hr. Preferably, flux-max/flux-min for the first two day period ranges from about 1 to about 8 ug/cm$^2$ hr, and flux-max/flux-min for the first three day period ranges from about 1 to about 8 ug/cm$^2$ hr. In certain preferable embodiments, the delivery rate from an inventive transdermal delivery system of 140 cm$^2$ ranges from about 140 to about 840 ug/hr (or from about 1 to about 6 ug/cm$^2$ hr) during the first 24 hour period (or time 0-24 hrs), programmed to deliver from about 140 to about 560 ug/hr (or from about 1 to about 4 ug/cm$^2$ hr) during 24-48 hours and designed to deliver from about 14 to about 420 ug/hr (or from about 0.1 to about 3 ug/cm$^2$ hr) from 48-72 hours. The bupivacaine fluxes and flux ranges above may be applicable for a wide variety of drug loadings in the inventive transdermal delivery systems.

The present transdermal delivery systems contain a sufficient amount of bupivacaine so that they may be used to induce and maintain a suitable state of analgesia in a subject for 3 or more days when applied to the skin of that subject. Other systems contain a sufficient amount of bupivacaine to induce and maintain a suitable state of analgesia in a subject for 5 or more days, while still others contain enough to induce and maintain a suitable state of analgesia in a subject up to 7 days.

A problem with a conventional local anesthetic transdermal delivery system, known as LidoDerm®, is that the patch can only be worn for 12 hours at a time according to the product labeling. This limitation is apparently due to the irritation caused by wearing of the transdermal delivery system, and insufficient adhesion of the thick hydrogel patch. In an embodiment of the present invention, transdermal delivery systems are provided that can be worn for prolonged periods, for instance 3 or more days, preferably 5 or more days, and more preferably for 7 or more days. Formulations for the present invention deploy synthetic polymers and additives of non-irritating and non-sensitizing kinds. For example, in an embodiment, the backing film is virgin polyester which is spun-laced into a non-woven fabric. Further, in an embodiment comprising polyisobutyrates ("PIBs"), low and high molecular weight PIBs are synthetic petroleum based polymers. In a preferred embodiment of the PIB embodiment, polybutenes of which the PSA is comprised are also synthetic petroleum based polymers. In an embodiment, the release liner is a siliconized polyester film, where a synthetic silicone oil is coated on a polyester film without using any extemporaneous binding or bonding agents. It is preferred to exclude from transdermal delivery systems of the present invention such known skin irritants and sensitizers as ionic surfactants, urea or its derivatives, ionizable polymers, propylene glycol, organic acids such as tartaric acid, and cross linking agents such as dihydroxyaluminum. As a comparator, the inventors believe that LidoDerm® has all of these skin damaging chemicals.

In embodiments, the inventive systems may be removed once applied and then reapplied and/or repositioned. This is a desirable quality in systems such as the inventive systems, which can be used to treat local pain disorders. In situations where the inventive systems are used to treat local disorders, it is important to apply the systems to a subject in such a way that the bupivacaine reaches the site of the locus of pain. If the system is incorrectly applied, then the subject will likely desire to reposition the system. If the incorrectly applied system cannot be repositioned, then it will be wasted. Repositionability therefore represents a means for reducing waste, and potentially improving treatment.

In certain circumstances, local pain disorders may be accompanied with localized skin disruptions. For instance, post-herpetic neuralgias may be preceded by or may occur simultaneously with a rash and open sores (e.g. shingles). For some patients, it may be appropriate to apply the inventive TDSs during periods of localized skin disruptions, often for periods of greater than 24 hours, preferably for about two days, more preferably for about three days. In such situations, it may be preferable to sterilize the inventive TDSs prior to application to a subject. This reduces the chance of communicating infective agents to the subject from the TDS via the localized skin disruption. In an embodiment, the inventive TDS is sterile. The inventive TDS may be sterilized using conventional sterilization methods useful in sterilizing transdermal delivery systems. In a preferred embodiment, the inventive TDS may be terminally sterilized using irradiative sterilization methods. In other embodiments, the inventive TDS may be terminally sterilized using gaseous techniques such as ethylene oxide sterilization. In further embodiments, the inventive TDS may be assembled from sterile components under aseptic conditions to achieve overall sterility.

In certain embodiments, it is desirable to control the amount of residual bupivacaine left in the inventive TDS following use. In embodiments, the residual amount of bupivacaine in the inventive TDS following a two day period of use ranges from about 20 wt % to about 85 wt %, based on the total weight of bupivacaine in the TDS prior to use. More preferably, residual amount of bupivacaine in the inventive TDS following a two day period of use ranges from about 30 wt % to about 75 wt %, based on the total weight of bupivacaine in the TDS prior to use. More preferably, residual amount of bupivacaine in the inventive TDS following a two day period of use ranges from about 40 wt % to about 60 wt %, based on the total weight of bupivacaine in the TDS prior to use. In an embodiment, the residual amount of bupivacaine in the inventive TDS following a three day period of use ranges from about 20 wt % to about 85 wt %, based on the total weight of bupivacaine in the TDS prior to use. More preferably, residual amount of bupivacaine in the inventive TDS following a three day period of use ranges from about 30 wt % to about 75 wt %, based on the total weight of bupivacaine in the TDS prior to use. More preferably, residual amount of bupivacaine in the inventive TDS following a three day period of use ranges from about 40 wt % to about 60 wt %, based on the total weight of bupivacaine in the TDS prior to use.

E. Indications

The inventive transdermal delivery systems comprising bupivacaine are useful in the treatment of a variety of conditions that involve localized pain. Some conditions that may be treatable using the inventive transdermal delivery systems comprise neuropathic pain such as but not limited to post-herpetic neuralgia; lower back pain; fibromyalgia; localized neuropathies including but not limited to diabetic neuropathies; complex regional pain disorder; joint pain; sports-induced injuries; sprains; strains; soft-tissue injury; repetitive motion injury; carpal tunnel syndrome; injury to tendons, ligament, and muscles; conditions such as fibromyalgia, bursitis, castrochondritis, and myofascial pain; pain associated with arthritis; inflammation; contusions; post-surgical pain; and nociceptive pain.

The number of transdermal delivery systems needed to treat a given condition can be determined conventionally, for example by titrating the number of patches that are applied to a region of a subject's body that presents with pain.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods within the scope of the invention, in addition to those enumerated herein, will be apparent to those skilled in the art from the foregoing description. Such modifications and variations are intended to fall within the scope of the appended claims. The present invention is to be limited only by the terms of the appended claims, along with the full scope of equivalents to which such claims are entitled.

F. Examples

Below are examples of specific embodiments for carrying out the present invention. The examples are offered for illustrative purposes only, and are not intended to limit the scope of the present invention in any way.

Examples 1-4

Bupivacaine Transdermal Patches with Different SAIB Concentration in the Formulations Monolithic bupivacaine transdermal delivery systems prepared according to the invention are as follows. Formulation recipes are shown in Table 2 below. Pre-weighed amounts of both high and low molecular weight PIBs, polybutene, and bupivacaine free base were added into glass vessels containing pre-measured amount of n-heptane and the containers were sealed. The sealed glass jar with excipients was placed onto a rotating wheel (Glas-Col Rugged Rotator) set at approximately 60 rpm. All the excipients in the sealed containers were completely dissolved in n-heptane at room temperature after constant mixing for 2-3 days.

Then, mixing action was stopped for approximately 15 minutes, and air bubbles were removed from the bupivacaine solution. The solution was cast into a 25 mil thick reservoir layer on a piece of release liner using a motorized film applicator (Elcometer, Inc.). The wet bupivaine solution films on the release liner section were air-dried for approximately 20 minutes at room temperature and 30 minutes at 70° C. in a convection oven (Blue M Electric, CSP Series Class A Oven). The oven dried bupivacaine films coated on the release liner were cooled to room temperature and a precut piece of the backing film was laminated onto the reservoir/release liner using a modified motorized film applicator (Elcometer, Inc.) to squeeze and eliminate air pockets out of the reservoir/release liner laminates.

Individual patches were die-cut from these laminates using steel rule dies (Apex Die, Inc.) and a punch press (Schmidt Press, Model 11V) into required system sizes to generate monolithic transdermal patches containing approximately 0.29 mg/cm² of bupivacaine base.

TABLE 2

| | B100 (w/w %) | B12 SFN (w/w %) | H100 (w/w %) | SAIB (w/w %) | Bupivacaine (w/w %) | B100/ B12 SFN | H100/ PIB |
|---|---|---|---|---|---|---|---|
| Example 1 | 18.1 | 22.3 | 56.6 | 0 | 3.0 | 0.81 | 1.4 |
| Example 2 | 17.9 | 22.1 | 56.0 | 1.0 | 3.0 | 0.81 | 1.4 |
| Example 3 | 17.7 | 21.9 | 55.4 | 2.0 | 3.0 | 0.81 | 1.4 |
| Example 4 | 17.1 | 21.2 | 53.7 | 5.0 | 3.0 | 0.81 | 1.4 |

Example 5

Bupivacaine Transdermal Patches with Indopol L14 as a Tackifier in the Formulation Monolithic bupivacaine transdermal delivery systems were prepared generally according to the methods as described in Examples 1-4 above and comprising Indopol L14 instead of H100 as a tackifier. The formulation recipes are shown in Table 3 below.

TABLE 3

| | B100 (w/w %) | B12 SFN (w/w %) | L14 (w/w %) | H100 (w/w %) | SAIB (w/w %) | Bupivacaine (w/w %) | B100/ B12 SFN | H100/ PIB |
|---|---|---|---|---|---|---|---|---|
| Example 5 | 21.7 | 26.8 | 46.0 | 0.0 | 2.0 | 3.5 | 0.81 | 0.95 |

Example 6-8

Bupivacaine Transdermal Patches with Different Bupivacaine Concentrations in the Formulations Monolithic bupivacaine transdermal delivery systems were prepared, generally according to the methods as described in Example 1-4 above. They comprised respectively 1 wt %, 2 wt %, and 3.5 wt % of bupivacaine. The formulation recipes are shown in Table 4.

TABLE 4

| | B100 (w/w %) | B12 SFN (w/w %) | H100 (w/w %) | SAIB (w/w %) | Bupivacaine (w/w %) | B100/ B12 SFN | H100/ PIB |
|---|---|---|---|---|---|---|---|
| Example 6 | 18.1 | 22.3 | 56.6 | 2.0 | 1.0 | 0.81 | 1.4 |
| Example 7 | 17.9 | 22.1 | 56.0 | 2.0 | 2.0 | 0.81 | 1.4 |
| Example 8 | 17.6 | 21.8 | 55.1 | 2.0 | 3.5 | 0.81 | 1.4 |

Example 9

In Vitro Bupivacaine Flux Through Human Skin

Figure 4:
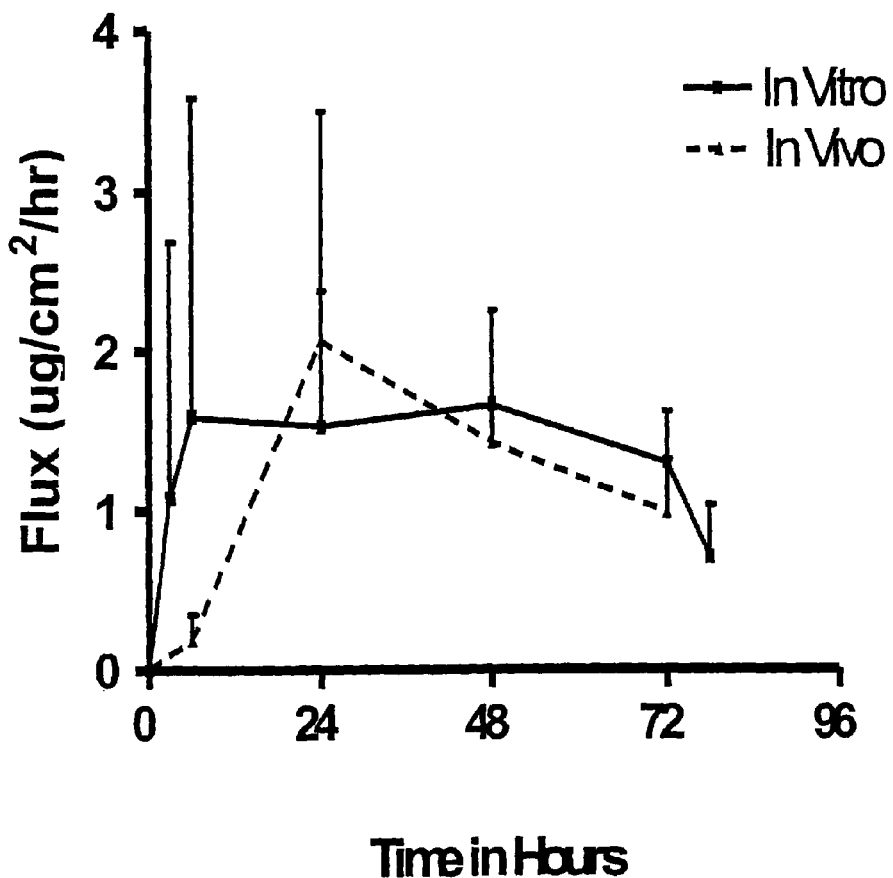
FIG. 4 shows in vivo and in vitro skin flux profile for embodiments of the inventive transdermal delivery system comprising buivacaine.

In-vitro permeation bupivacaine flux studies were conducted with human skin from cadaver donors (dermatomed full thickness) using transdermal monolithic bupivacaine patches. The monolithic bupivacaine patches containing 0.29 mg/cm² of bupivacaine free base for a 1.42 cm² patch were prepared generally according to the methods described in Examples 1-4 with a recipe of 17.1 wt % of Oppanol®B100, 21.2 wt % of Oppanol®B12 SFN, 53.7 wt % of Indopol H100, 5.0 of wt % SAIB and 3.0 wt % of bupivacaine. Thigh skin from nine different donors was used in the experiments, with a minimum of 5 replicate skin samples per donor (total n=57). Prior to the in vitro skin drug flux experiment, the skin tissue was examined under a magnifying glass for any defects such as pinholes. Excluding any damaged areas, the intact skin areas were cut into 1-inch circles. In the tests, a bupivacaine transdermal delivery system was placed on the stratum corneum side of the pre-cut skin sample. Then, the assembly of system and pre-cut skin specimen was positioned on the top edge of the receptor side of a modified Franz cell with the dermal side of the skin tissue facing the receptor chamber. The donor side of the Franz Cell was securely positioned over the skin/system assembly, and the receptor chamber was filled with PBS buffer at pH 7.4 containing 0.01% sodium azide. The Franz cell with the test system was equilibrated at 32° C. for the duration of the experiment. At predetermined intervals (typically 3 hours, 6 hours, 1, 2, and 3 days), the entire receptor solution was collected from the Franz cell and refilled with fresh receptor medium. The receptor solutions were assayed for bupivacaine concentration using a HPLC chromatographic method. The cumulative delivery amount and skin drug flux were calculated for each skin/test system assembly. FIG. 4 illustrates the actual bupivacaine skin flux over 3 days through human cadaver specimens from the 9 different donors, plotted with in vivo data from Example 11. The overall average bupivacaine skin flux was approximately 1.6 $\mu g/cm^2/hr$, with a coefficient of variation of 40%.

with 0.1% Sodium Dodecyl Sulfate pH 5.5 buffer solution was placed in the vessels and maintained at 32° C. while the stainless steel cylinder rotational speed was maintained at 50 rpm during the dissolution experiment.

At the preset time intervals of 0.5, 1, 2, 4, 8, 12, 16, 24, 30, and 36 hours; 1 mL portions of the dissolution medium were withdrawn from the vessels and dispensed into HPLC vials. The following conditions were used for the bupivacaine assay in the samples:

Mode: Isocratic
Mobile Phase: A—60% $(NH_4)_2HPO4$ at pH 6.7±0.05
  B—40% 100% acetonitrile
Run Time: 8.0 minutes
Column: Zorbax Eclipse XDB C8, 4.6×50 mm, 3.5 µm
Column Temperature: 40° C.
Flow Rate: 1.0 mL/min
UV Detection: 225 nm
Injection Volume: 10 µL
Retention time of Bupivacaine: Between 5-6 minutes From the bupivacaine concentration, total volume of the buffer solution remaining in the vessels and time intervals, it was possible to calculate the cumulative amounts of bupivacaine dissolved or released from the patches over time, and dissolution rate or release rate of bupivacaine from the sample transdermal delivery systems were calculated.

Figure 5:
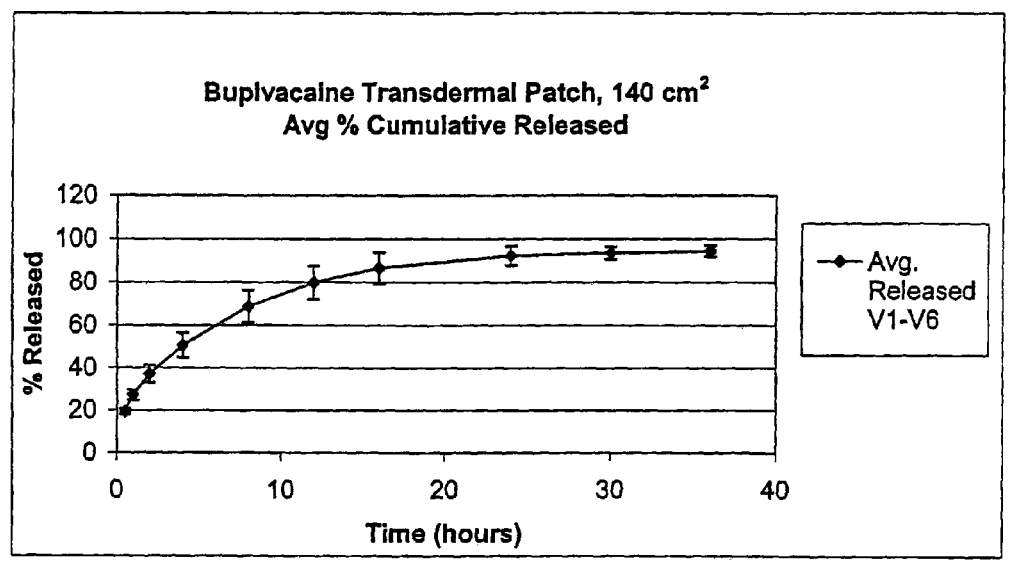
FIG. 5 shows results from dissolution rate testing for embodiments of the inventive transdermal delivery system comprising buivacaine.

The results from the dissolution rate test are shown in FIG. 5, and provided below in Table 5.

TABLE 5

| Sampling Time (hours) | Cumulative Amount of Bupivacaine Released (mg) Vessel 1 | Cumulative Amount of Bupivacaine Released (mg) Vessel 2 | Cumulative Amount of Bupivacaine Released (mg) Vessel 3 | Cumulative Amount of Bupivacaine Released (mg) Vessel 4 | Cumulative Amount of Bupivacaine Released (mg) Vessel 5 | Cumulative Amount of Bupivacaine Released (mg) Vessel 6 | Average (mg) | SD | % Cumulative Release Rate (n = 6) |
|---|---|---|---|---|---|---|---|---|---|
| 0.5 | 7.401 | 7.650 | 9.730 | 7.654 | 7.117 | 9.218 | 8.129 | 1.1 | 19 ± 3 |
| 1 | 10.13 | 10.62 | 14.35 | 10.29 | 9.746 | 13.59 | 11.46 | 1.9 | 27 ± 5 |
| 2 | 13.60 | 14.71 | 19.17 | 13.53 | 13.49 | 19.01 | 15.58 | 2.8 | 37 ± 7 |
| 4 | 18.48 | 20.66 | 25.25 | 18.46 | 19.25 | 25.52 | 21.27 | 3.3 | 50 ± 8 |
| 8 | 25.63 | 28.93 | 32.84 | 26.17 | 27.19 | 33.08 | 28.97 | 3.3 | 69 ± 8 |
| 12 | 31.17 | 34.14 | 36.34 | 31.13 | 31.89 | 37.08 | 33.63 | 2.6 | 80 ± 6 |
| 16 | 35.51 | 37.70 | 38.07 | 34.05 | 34.93 | 38.94 | 36.53 | 2.0 | 87 ± 5 |
| 24 | 38.82 | 39.71 | 39.13 | 37.15 | 37.87 | 40.64 | 38.87 | 1.3 | 92 ± 3 |
| 30 | 39.68 | 40.15 | 39.26 | 38.34 | 38.18 | 40.84 | 39.41 | 1.0 | 94 ± 2 |
| 36 | 39.90 | 10.35 | 39.67 | 38.78 | 38.76 | 41.28 | 39.79 | 1.0 | 94 ± 2 |

Example 10

Bupivacaine Dissolution Test on Transdermal Delivery System

A bupivacaine transdermal delivery system having a drug releasing interface surface area of 140 cm² Monolithic adhesive matrix patches, using a high molecular weight/low molecular weight polyisobutylene (PIB) blend for the adhesive and containing 0.29 mg/cm2 of bupivacaine were prepared generally according to the methods as described in Examples 1-4 above with a recipe comprising 17.1 wt % of Oppanol®B100, 21.2 wt % of Oppanol®B12 SFN, 53.7 wt % of Indopol H100, 5.0 wt % of SAIB and 3.0 wt % of bupivacaine.

In the test, the bupivacaine transdermal delivery system was held adhesively on a stainless steel cylinder, having the drug releasing surface of the patch facing outward and immersable in release medium, and positioned at the center of a USP Dissolution Apparatus II with 1 L vessels. Next, 1000 mL of degassed dissolution media 0.005N sodium phosphate Example 11

Human Pharmacokinetic Trials

A pharmacokinetic study was performed in healthy volunteers (4 females and 4 males) to evaluate transdermal delivery systems according to the invention. The reference therapy was a 2 mg/hour infusion of bupivacaine for 4 hours and was compared to the inventive transdermal delivery systems to evaluate the in-vivo performance of these inventive system. The study was performed as follows. Subjects first received the reference infusion therapy. Following a washout period, each subject received an inventive transdermal delivery system, made according to the recipe of Example 4. In Part 1 of the study, two inventive 140 cm² transdermal delivery systems containing approximately 40.9 mg bupivacaine per TDS were applied and then replaced each day for three consecutive days. In Part 2, following a washout period, one inventive 140 cm² transdermal delivery system containing approximately 40.95 mg bupivacaine was applied to the subjects and then maintained in place for three days. Six patients completed Part 2 (3 females and 3 males).

Following each treatment, serial blood samples for the determination of plasma bupivacaine concentrations were collected at various time points, as laid out in Tables 6 and 7.

Additionally, skin condition at the application site was noted for both Part 1 and Part 2 of the study. The most common skin condition-related adverse event was contact dermatitis at the application site (i.e. erythema) upon removal of the TDSs. Mild erythema was observed in 8 out of 8 (100%) subjects in Part 1 of the study, and 1 out of 6 subjects (16.7%) in Part 2. This data indicates that frequent applications and removals of TDSs without resting periods results in greater skin irritation, while continuous application of TDSs for 3 days produced a lesser dermal response than daily application and removal of the TDSs, while maintaining plasma concentrations of bupivacaine throughout 3 days. Additionally, the data suggest that, despite bupivacaine's relatively high Log P (as compared to other local anesthetics such as lidocaine), transdermal delivery of bupivacaine is associated with an acceptable level of skin irritation.

TABLE 6

Reference Phase and Part 1

| Study Day | Study Phase | Plasma Samples |
|---|---|---|
| Day 0 | 4-hour Bupivacaine Infusion | 14 samples at: −0.5 hours (30 minutes before the start of infusion), and at 1, 2, 3, 4, 4.5, 5, 6, 6.5, 7, 8, 10, 12, and 16 hours after start of bupivacaine infusion |
| Day 1 | Application of First Bupivacaine TTS | samples at: 0 hours (to be taken immediately prior to application of first Bupivacaine TTS), and at 4, 8, 12 and 16 hours after application of first Bupivacaine TTS |
| Day 2 | Application of Second Bupivacaine TTS | samples at 24 hours after first TTS application (to be taken immediately prior to removal of first Bupivacaine TTS), and at 4, 8, 12, and 16 hours after application of second Bupivacaine TTS. No greater than 30 min shall elapse between removal of previous Bupivacaine TTS and application of the next. |
| Day 3 | Application of Third Bupivacaine TTS | 6 samples at 24 hours after second TTS application (to be taken immediately prior to removal of second Bupivacaine TTS), and at 4, 8, 12 and 16 hours after application of third Bupivacaine TTS. No greater than 30 min shall elapse between removal of previous Bupivacaine TTS and application of the next. |
| Day 4 | Removal of Third Bupivacaine TTS | samples at: 0 hours (to be taken immediately prior to removal of the third Bupivacaine TTS), and at 1, 3, 6, 12, and 16 hours after removal of third Bupivacaine TTS |

TABLE 6-continued

Reference Phase and Part 1

| Study Day | Study Phase | Plasma Samples |
|---|---|---|
| Day 5 | Study End | samples at: 24, 32, and 40 hours after removal of third pair of Bupivacaine TTS |

TABLE 7

Part 2

| Study Day | Study Phase | Plasma Samples |
|---|---|---|
| Day 0 | Application of Bupivacaine TTS | samples at: 0 hours (to be taken immediately prior to application of first Bupivacaine TTS), and at 4, 8, 12 and 16 hours after application of Bupivacaine TTS |
| Day 1 | Completion of First Bupivacaine TTS Wearing Day | samples at: 24, 30, 36, and 40 hours after application of Bupivacaine TTS |
| Day 2 | Completion of Second Bupivacaine TTS Wearing Day | samples at: 48, 54, 60, and 64 hours after application of Bupivacaine TTS |
| Day 3 | Removal of Bupivacaine TTS | samples at: 72, 78, and 84 hours after application of Bupivacaine TTS |
| Day 4 | Study End | sample at: 96 hours after application of Bupivacaine TTS |

Figure 6:
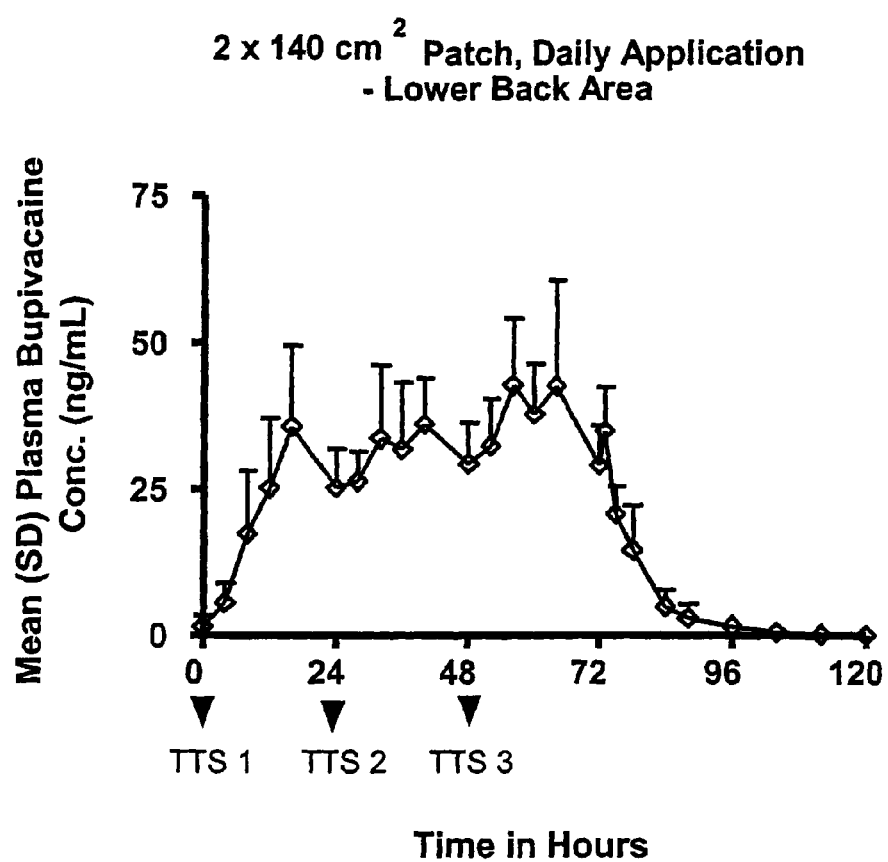
FIG. 6 shows a concentration vs. time plot for Part 1 of Example 11.
Figure 7:
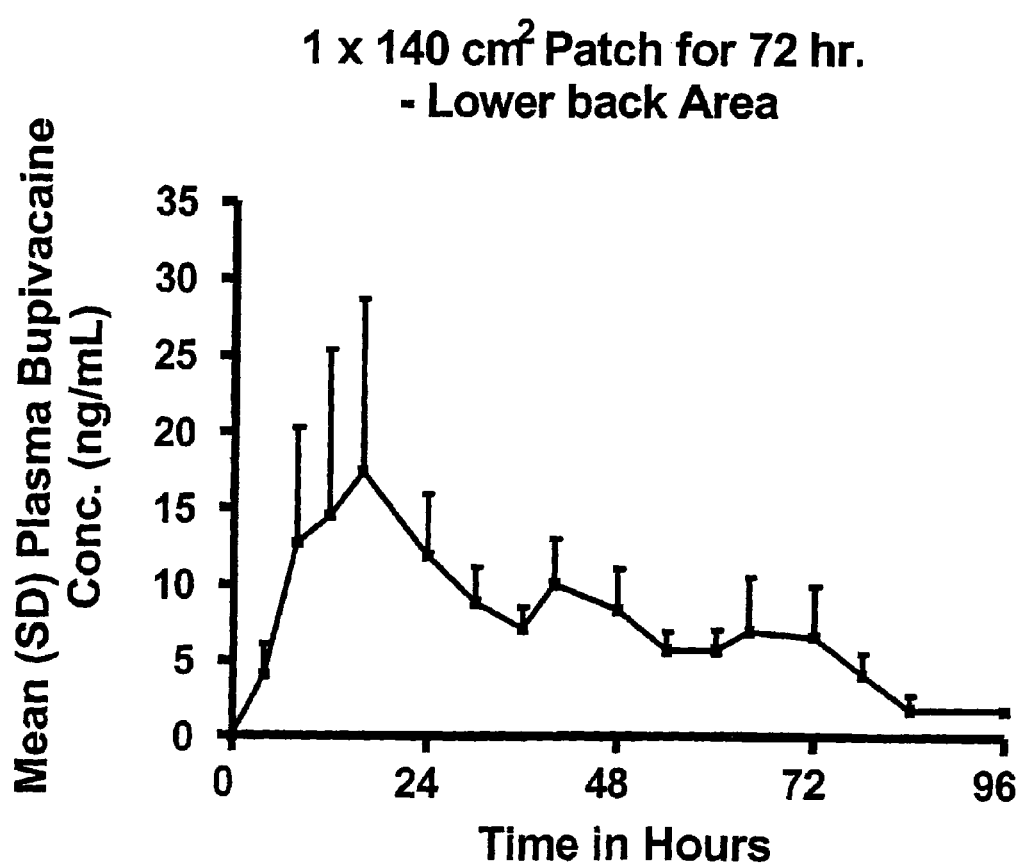
FIG. 7 shows a concentration vs. time plot for Part 2 of Example 11.

The results are shown in Tables 8 and 9, and in FIGS. 6 and 7. FIG. 4 shows calculated in vivo flux for inventive TDSs, plotted against in vitro flux data. Tmax is shown in units of hours, Cmax is in units of ng/ml, AUClast and AUC0-24 is in units of ng-hr/ml. 24 hr % and 24-48 hr % represent percent of total AUC present between 0-24 hours following dosing and 24-48 hours following dosing, respectively. From a single patch application over 72 hours, a mean maximum plasma concentration of 19.9 ng/mL was reached at a median of 16 hours following initial dosing, and gradually declining to ~5 ng/mL by 72 hours with no surge or depot effects noted. The bupivacaine plasma concentrations decline after TDS removal with a terminal half-life of approximately 6 hours.

TABLE 8

Part 1 - PK Data (2 patches q 24 hr)

| Subject | Tmax | Cmax | AUClast | AUC0-24 | AUC (24-48) | 24 hr % | 24-48 hr % |
|---|---|---|---|---|---|---|---|
| 101 | 16 | 58.7 | 2619.19 | 718.07 | 859.45 | 27.42 | 32.81 |
| 102 | 12 | 30.9 | 1928.01 | 472.71 | 610.22 | 24.52 | 31.65 |
| 103 | 12 | 31.2 | 2178.14 | 543.61 | 629.77 | 24.96 | 28.91 |
| 104 | 16 | 32.7 | 2629.35 | 554.11 | 768.5 | 21.07 | 29.23 |
| 201 | 24 | 18.6 | 2068.51 | 214.79 | 674.44 | 10.38 | 32.61 |
| 202 | 16 | 34.5 | 2199.76 | 411.88 | 731.18 | 18.72 | 33.24 |
| 203 | 16 | 36.4 | 1964.47 | 393.84 | 662.45 | 20.05 | 33.72 |
| 204 | 16 | 50.4 | 3262.16 | 738.88 | 1067.1 | 22.65 | 32.71 |
| Mean | 16.00 | 36.68 | 2356.20 | 505.99 | 750.39 | 21.22 | 31.86 |
| SD | 3.70 | 12.44 | 453.60 | 173.32 | 151.47 | 5.21 | 1.82 |
| CV % | 23.15 | 33.93 | 19.25 | 34.25 | 20.19 | 24.57 | 5.72 |
| Min. | 12.00 | 18.60 | 1928.01 | 214.79 | 610.22 | 10.38 | 28.91 |
| Max. | 24.00 | 58.70 | 3262.16 | 738.88 | 1067.10 | 27.42 | 33.72 |

* Cmax & Tmax derived from 0-24 hr

TABLE 9

Part 2 (One patch for 72 hours)

| Subject | Tmax | Cmax | AUClast | AUCinf | AUC (0-24) | AUC (24-48) | 24 hr % | 24-48 hr % |
|---|---|---|---|---|---|---|---|---|
| 101 | 16.00 | 18.20 | 572.88 | 581.20 | 230.48 | 186.59 | 40.23 | 32.57 |
| 102 | 8.00 | 19.90 | 637.68 | 646.41 | 270.52 | 199.25 | 42.42 | 31.25 |
| 103 | 12.00 | 21.70 | 730.12 | 746.04 | 313.13 | 218.13 | 42.89 | 29.88 |
| 201 | 64.00 | 13.90 | 641.08 | 663.27 | 45.62 | 218.75 | 7.12 | 34.12 |
| 203 | 24.00 | 12.70 | 487.85 | 541.47 | 151.52 | 183.04 | 31.06 | 37.52 |
| 204 | 16.00 | 33.10 | 1007.01 | NA | 505.65 | 293.54 | 50.21 | 29.15 |
| Mean | 23.33 | 19.92 | 679.44 | 635.68 | 252.82 | 216.55 | 35.65 | 32.41 |
| SD | 20.62 | 7.32 | 179.53 | 78.90 | 155.93 | 40.63 | 15.27 | 3.08 |
| CV % | 88.36 | 36.77 | 26.42 | 12.41 | 61.68 | 18.76 | 42.84 | 9.51 |
| Min. | 8.00 | 12.70 | 487.85 | 541.47 | 45.62 | 183.04 | 7.12 | 29.15 |
| Max. | 64.00 | 33.10 | 1007.01 | 746.04 | 505.65 | 293.54 | 50.21 | 37.52 |

Example 12

Peel Force Comparison

Two formulations were prepared, using methods generally according to Examples 1-4, according to the following recipe in Table 10:

TABLE 10

| Formulation | 0% SAIB | 5% SAIB |
|---|---|---|
| Oppanol B100 poly iso-butylene | 18.1 | 17.1 |
| poly iso-butylene poly iso-butylene Oppanol B12 poly iso-butylene | 22.3 | 21.2 |
| Indopol H100 polybutylene | 56.6 | 53.7 |
| Sucrose acetate Isobutyrate | 0.0 | 5.0 |
| Bupivacaine base | 3.0 | 3.0 |

Weight percentages are based on the total weight of the formulation as listed.

The formulations were then tested for 90° adhesion force to a steel plate. In order to measure 90° adhesion force to a steel plate, test laminates of the two above formulations were cut into 1" wide and 6" long strips. Next, the release liner was removed. The adhesive side of the test laminates was placed on a clean steel plate and pressed firmly by a roller several times. One end of the backing film of the test laminate was gripped with a sample holder and was peeled off at 90° to the steel plate at various speeds using an (mass slip/peel tester (Model SP-2000). The observed adhesion force values were averaged for 5-20 seconds depending on the speed, with a specified delay (after peeling started but before data collection began).

Figure 8:
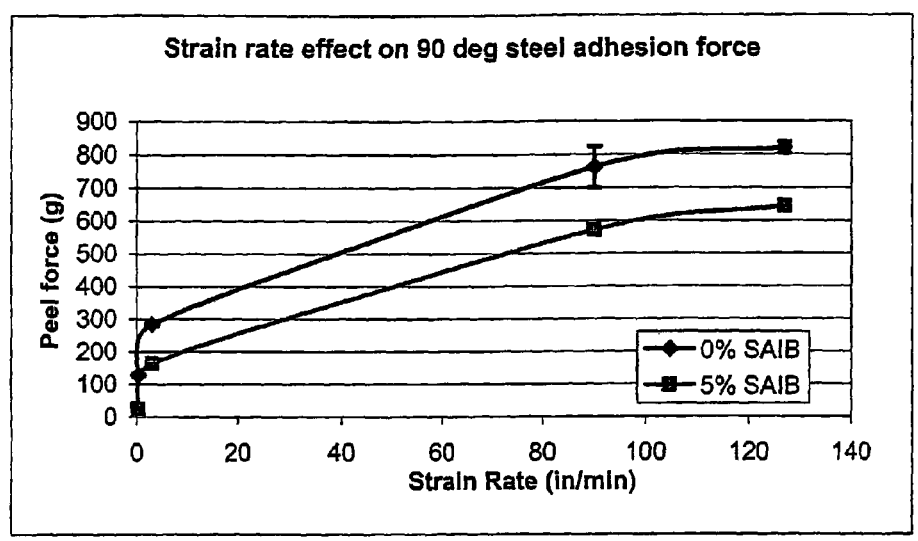
FIG. 8 shows a plot of the strain effect on 90 degree steel adhesion force for various embodiments of the present invention.

Test conditions were as follows:

1. 0.3 ins/min speed: 4 seconds delay time and 50 second averaging time
2. 3 ins/min speed: 4 seconds delay time and 20 second averaging time
3. 90 ins/min speed: 0.1 seconds delay time and 5 second averaging time
4. 127 ins/min speed: 0.1 seconds delay time and 5 second averaging time Results are shown in Table 11, and in FIG. 8.

TABLE 11

90 steel adhesion force of Bupivacaine laminates

| | 0% SAIB | 5% SAIB |
|---|---|---|
| 0.3 inch/min. | 128 ± 4 (g) | 25 ± 6 (g) |
| 3 inch/min. | 284 ± 6 (g) | 164 ± 7 (g) |
| 90 inch/min. | 762 ± 62 (g) | 572 ± 13 (g) |
| 127 inch/min. | 820 ± 17 (g) | 644 ± 19 (g) |

Example 13

Clinical Trial (Interim Analysis)

A double-blind, placebo controlled, two arm cross-over, multicenter trial in patients with neuropathic pain due to post-herpetic neuralgia (PHN) in the thoracic or lumbar region was performed. Subjects were to receive two treatments in a randomly assigned sequence: one treatment with three Bupivacaine TTS patches and one with three Placebo Bupivacaine TTS patches. Each treatment period was to last 3 days with a washout period of approximately 3-14 days between treatment periods in order to allow the subject's pain intensity to return to the baseline level prior to application of the second set of patches. Subjects whose pain intensity did not return to baseline level by 14 days were not continued in the trial.

Active TDSs were bupivacaine TDSs according to the invention with 3 wt % bupivacaine base, and a 140 cm2 TDS size. Three TDSs were applied to the area of maximum pain. Placebo TDSs were the same area (140 cm2) as the active TDSs. Three placebo patches were applied to the area of maximum pain, with the same treatment cycle as the active arms.

A total of 36 subjects were included in an interim analysis of the trial. The purpose of the interim analysis was to describe the safety and activity of the drug. Inferential statistics were not pursued since this was an exploratory study and the interim analysis comprised a small sample size. Instead, the interim analysis was directed towards identifying possible trends in the data.

The following efficacy related endpoints were measured and analyzed (in accordance with the protocol pre-specification) as part of the interim analysis: (1) Mean daily pain intensity, measured by an 11-point Numeric Rating Scale (PI-NRS) (DC Turk et al., Neglected topics in chronic pain treatment outcome studies: determination of success, Pain.

53(1):3-16 (April 1993)) as an average of measurements in the morning, afternoon and evening; (2) Subject's global impression of change (SGIC), a 7-point categorical scale; (3) Proportion of subjects achieving at least a 20% improvement (relative to baseline) in terms of mean daily pain intensity as measured by PI-NRS; and (4) Rescue medications usage. Both the PI-NRS and the PGIC have been used in clinical trials for PHN to establish a clinically important difference in pain intensity. J T Farrar et al., Clinical importance of changes in chronic pain intensity measured on an 11-point numerical pain rating scale, Pain. 94(2):149-58 (November 2001). The trial protocol called for subjects to have had an initial PI-NRS score from 4-9 to be included in the trial. Additionally, certain safety signals were analyzed as part of the interim analysis, particularly skin and subcutaneous tissue disorders (reported as adverse events).

Rescue medications were made available to subjects in the event of break-through pain. Pain intensity was supposed to be greater than 5 on the PI-NRS for any rescue therapy.

Figure 10:
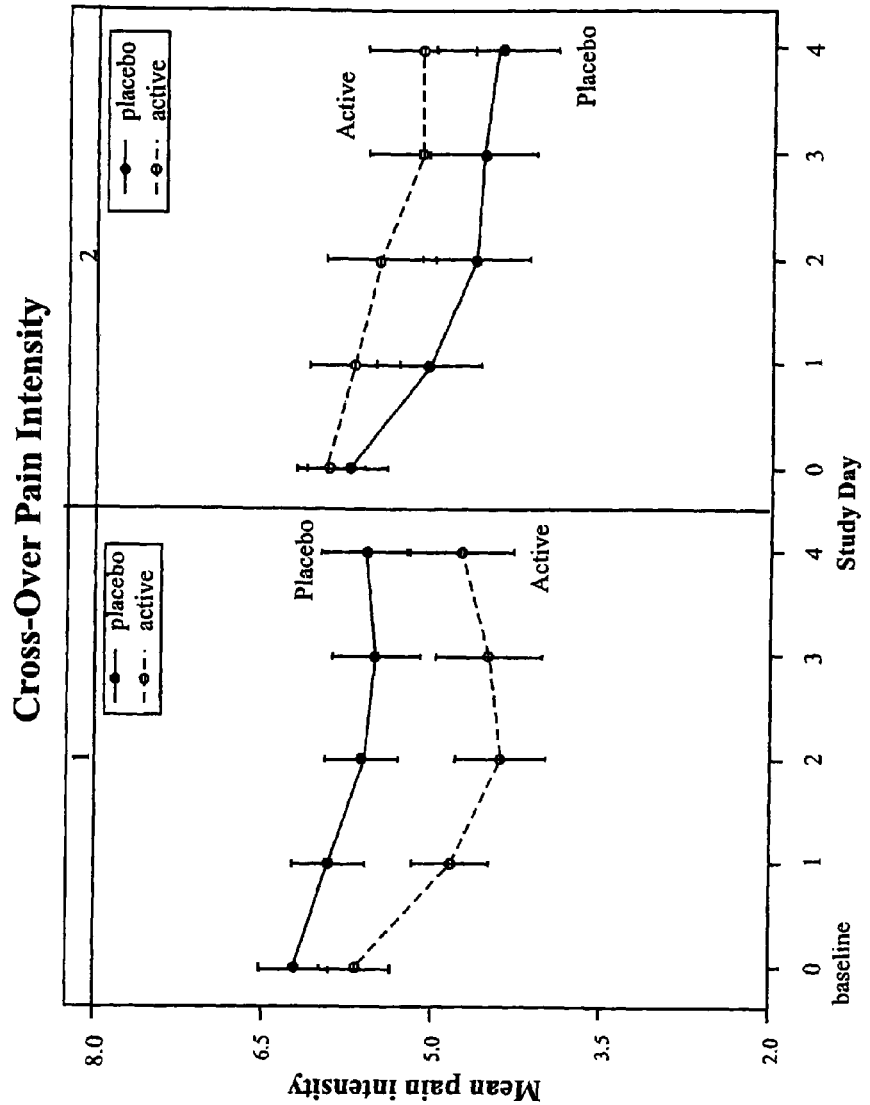
FIG. 10 shows a plot of Cross-Over Pain Intensity scores by period.
Figure 11:
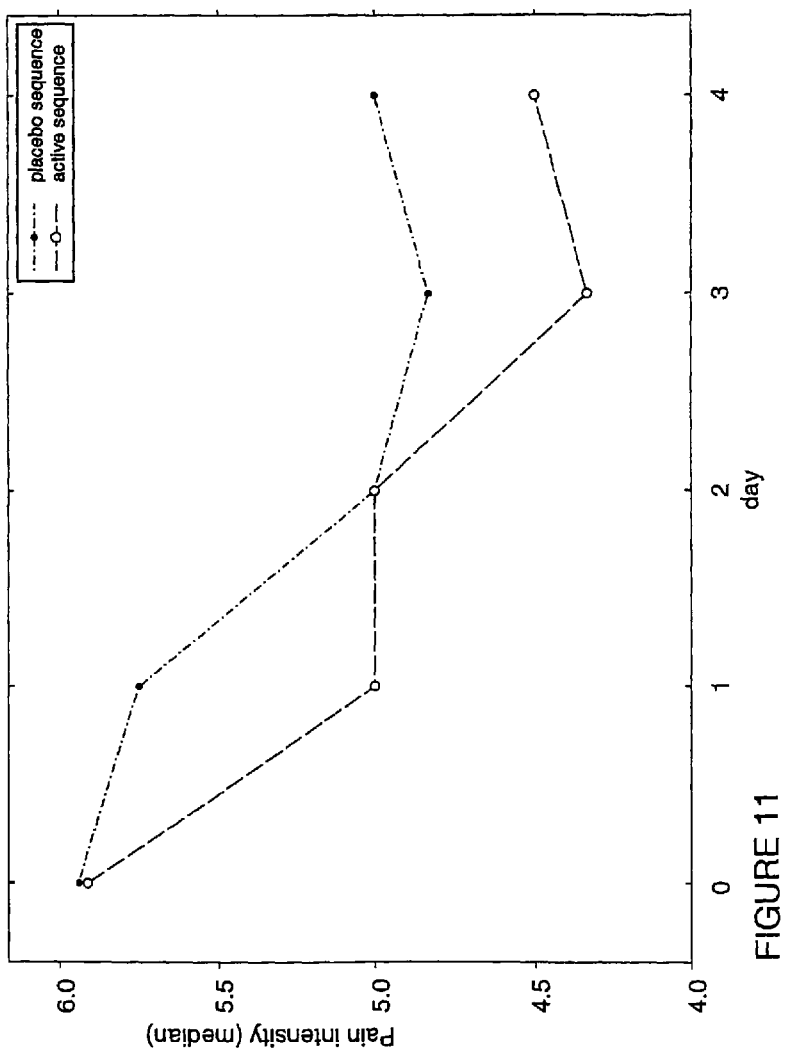
FIG. 11 shows a plot of Median Pain Intensity by Treatment Group.

The PI-NRS results are given in Table 12. The data from the PI-NRS results are plotted in FIGS. 9-11. FIG. 10 shows cross over pain intensity using the PI-NRS data, plotted by period. While the Period 1 data shows that subjects in the active arm suffer from less pain than subjects in the placebo arm, the Period 2 data however does not seem to confirm this trend. The difference between the Period 1 and Period 2 results may be characteristic of cross-over design and efficacy studies, such as this study. See generally S. Senn, Cross-over Trials in Clinical Research, John Wiley & Sons (2002); and J. Whitehead The Design and Analysis of Sequential Clinical Trials, John Wiley & Sons (1997). When the PI-NRS data was analyzed in accordance with the pre-specified analysis method (at the study level, irrespective of period, and by treatment sequence), as shown in FIG. 9, the results show a beneficial trend in favor of subjects on the active arm having lower pain PI-NRS scores than subjects on placebo. FIG. 11 shows median Pain Intensity (PI-NRS) scores by treatment group.

TABLE 12

PI-NRS Results

| Study Arm | Period | Day | n | Mean | Median | Std Err |
| --- | --- | --- | --- | --- | --- | --- |
| Active/Placebo | 1 | 0 | 16 | 5.663194 | 5.638889 | 0.31862 |
| Active/Placebo | 1 | 1 | 16 | 4.8125 | 4.5 | 0.335022 |
| Active/Placebo | 1 | 2 | 16 | 4.375 | 4.5 | 0.404689 |
| Active/Placebo | 1 | 3 | 16 | 4.46875 | 4.333333 | 0.46528 |
| Active/Placebo | 1 | 4 | 16 | 4.71875 | 4.5 | 0.46986 |
| Active/Placebo | 2 | 0 | 14 | 5.727778 | 5.75 | 0.361722 |
| Active/Placebo | 2 | 1 | 14 | 5 | 5.75 | 0.459933 |
| Active/Placebo | 2 | 2 | 14 | 4.583333 | 4.333333 | 0.47294 |
| Active/Placebo | 2 | 3 | 14 | 4.52381 | 4.5 | 0.464837 |
| Active/Placebo | 2 | 4 | 14 | 4.392857 | 4 | 0.540092 |
| Placebo/Active | 1 | 0 | 19 | 6.200877 | 5.944444 | 0.293796 |
| Placebo/Active | 1 | 1 | 19 | 5.894737 | 6 | 0.325745 |
| Placebo/Active | 1 | 2 | 19 | 5.596491 | 5.666667 | 0.323017 |
| Placebo/Active | 1 | 3 | 19 | 5.473684 | 5.333333 | 0.389361 |
| Placebo/Active | 1 | 4 | 19 | 5.561404 | 5.5 | 0.39638 |
| Placebo/Active | 2 | 0 | 18 | 5.887654 | 5.988889 | 0.307759 |
| Placebo/Active | 2 | 1 | 18 | 5.666667 | 5.75 | 0.396059 |
| Placebo/Active | 2 | 2 | 18 | 5.425926 | 5.333333 | 0.481921 |
| Placebo/Active | 2 | 3 | 18 | 5.055556 | 4.5 | 0.490468 |
| Placebo/Active | 2 | 4 | 18 | 5.074074 | 4.75 | 0.472025 |

Figure 12:
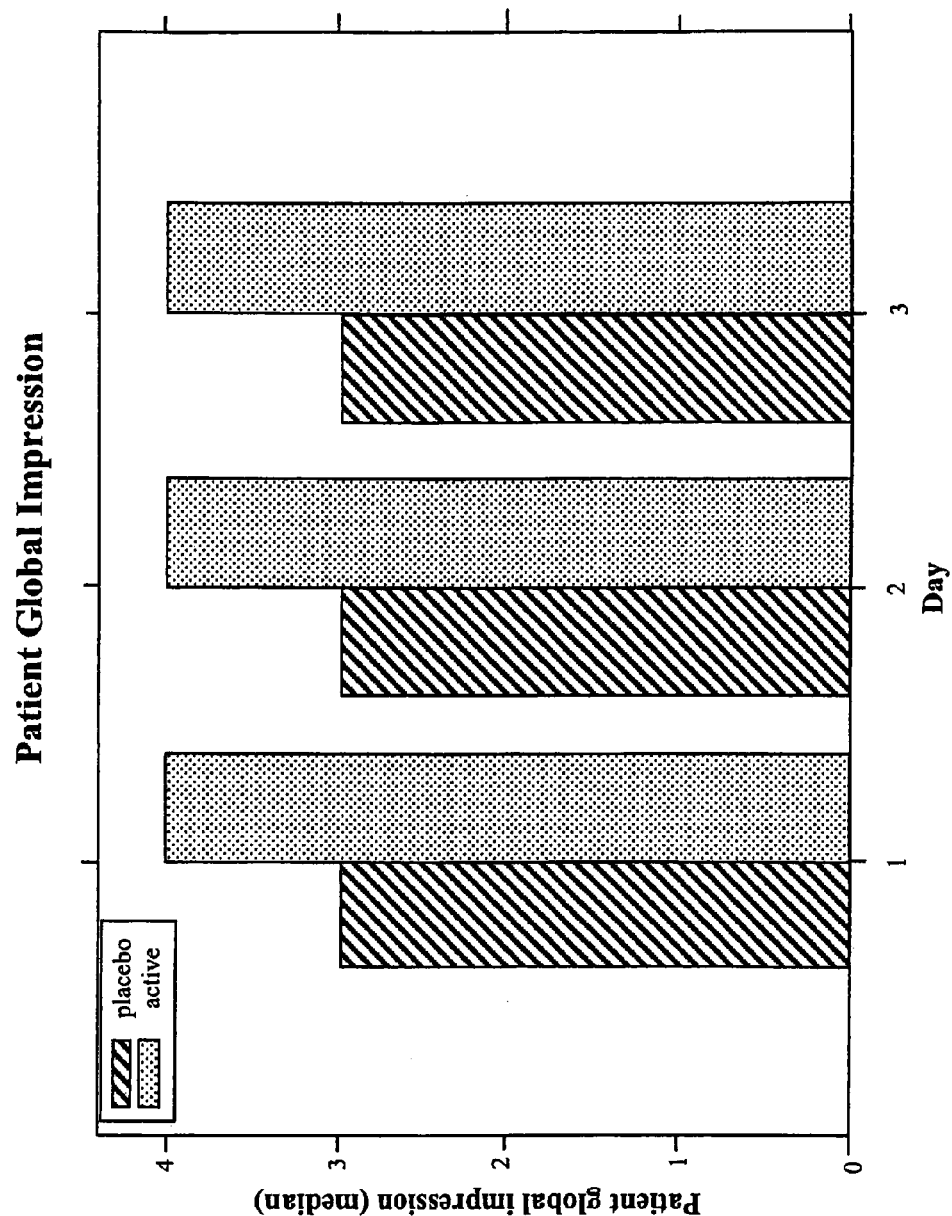
FIG. 12 shows a bar chart of median Patient Global Impression of Change scores.

Results from assessments of the SGIC are provided in FIG. 12. These data suggest a trend that subjects on the active arm had a one point better global impression than patients on placebo. This suggests that subjects on the active arm felt better and felt that their pain was better controlled.

The proportion of subjects achieving at least a 20% improvement (relative to baseline) in terms of mean daily pain intensity is shown in Table 13 below. The difference between the proportion of subjects achieving at least a 20% improvement was 51.5% for placebo and 62.9% for active. The proportion of subjects achieving at least a 20% improvement was greater for subjects on the active treatment arm (nearly two-thirds of subjects) than for placebo.

TABLE 13

Pain Reduction (20% or more improvement)

| Subjects with Pain Intensity Improvement | Placebo (n = 33) | Inventive TDS (n = 35) |
| --- | --- | --- |
| <20% | 16 (48.5%) | 12 (34.3%) |
| >=20% | 17 (51.5%) | 22 (62.9%) |

Only three subjects required rescue medication. All three subjects were in the active treatment arm at the time that they took the rescue medication, although one patient took rescue medication during both the placebo and active treatment arms of the stuff. These results were not meaningful as to supporting or contradicting efficacy of the inventive TDS.

The results of assessing skin and subcutaneous tissue disorders are shown in Table 14. As can be seen, the skin and subcutaneous tissue disorders adverse event rate was about three times higher for placebo than it was for the inventive TDS.

TABLE 14

Skin and Subcutaneous Tissue Disorder

| Treatment Group | Placebo (in %) | Inventive TDS (in %) |
| --- | --- | --- |
| Rash | 6.1 | 0 |
| Cold Sweat | 0 | 2.9 |
| Contact Dermatitis | 3 | 0 |
| Erythema | 3 | 0 |
| Total | 9.1 | 2.9 |

G. Additional Disclosure

1. A method comprising:
applying to a subject a transdermal delivery system that comprises bupivacaine;
transdermally delivering the bupivacaine from the transdermal delivery system for a period to the subject such that the following mean plasma concentrations are achieved:
a mean plasma concentration, normalized to an initial loading of the transdermal delivery system, ranging from about 0.0003 to about 0.7 cm2/L at about 12 hours after initiation of the transdermal delivery; and
a mean plasma concentration, normalized to an initial loading of the transdermal delivery system, ranging from about 0.0014 to about 0.4 cm2/L at about 24 hours after initiation of the transdermal delivery.

2. The method of claim 1, wherein the following mean plasma concentration is further achieved: a mean plasma concentration, normalized to an initial loading of the transdermal delivery system, ranging from about 0.0013 to 0.3 $cm^2/L$ at about 48 hours after initiation of the transdermal delivery.

3. The method of claim 1, wherein the following mean plasma concentration is further achieved: a mean plasma concentration, normalized to an initial loading of the transdermal delivery system, ranging from about 0.001 to 0.31 cm²/L at about 72 hours after initiation of the transdermal delivery.

4. The method of claim 1, wherein the following mean plasma concentration are achieved:

a mean plasma concentration, normalized to an initial loading of the transdermal delivery system, ranging from about 0.003 to about 0.07 cm2/L at about 12 hours after initiation of the transdermal delivery; and a mean plasma concentration, normalized to an initial loading of the transdermal delivery system, ranging from about 0.014 to about 0.04 cm2/L at about 24 hours after initiation of the transdermal delivery.

5. The method of claim 4, wherein the following mean plasma concentration is further achieved: a mean plasma concentration, normalized to an initial loading of the transdermal delivery system, ranging from about 0.013 to 0.03 cm²/L at about 48 hours after initiation of the transdermal delivery.

6. The method of claim 4, wherein the following mean plasma concentration is further achieved: a mean plasma concentration, normalized to an initial loading of the transdermal delivery system, ranging from about 0.01 to 0.031 cm²/L at about 72 hours after initiation of the transdermal delivery.

7. The method of claim 1, wherein the period is about two days.

8. The method of claim 7, wherein a residual amount of bupivacaine in the transdermal delivery system following the two day period of use ranges from about 20 wt % to about 85 wt %, based on the total weight of bupivacaine in the transdermal delivery system prior to transdermal delivery.

9. The method of claim 8, wherein a residual amount of bupivacaine in the transdermal delivery system following the two day period of use ranges from about 30 wt % to about 75 wt % based on the total weight of bupivacaine in the transdermal delivery system prior to transdermal delivery.

10. The method of claim 9, wherein a residual amount of bupivacaine in the transdermal delivery system following the two day period of use ranges from about 40 wt % to about 60 wt % based on the total weight of bupivacaine in the transdermal delivery system prior to transdermal delivery.

11. The method of claim 1, wherein the period is about three days.

12. The method of claim 11, wherein a residual amount of bupivacaine in the transdermal delivery system following the three day period of use ranges from about 20 wt % to about 85 wt %, based on the total weight of bupivacaine in the transdermal delivery system prior to transdermal delivery.

13. The method of claim 12, wherein a residual amount of bupivacaine in the transdermal delivery system following the three day period of use ranges from about 30 wt % to about 75 wt % based on the total weight of bupivacaine in the transdermal delivery system prior to transdermal delivery.

14. The method of claim 13, wherein a residual amount of bupivacaine in the transdermal delivery system following the three day period of use ranges from about 40 wt % to about 60 wt % based on the total weight of bupivacaine in the transdermal delivery system prior to transdermal delivery.

15. The method of claim 1, wherein the transdermal delivery system comprises a pressure sensitive adhesive.

16. The method of claim 15, wherein the pressure sensitive adhesive comprises polyisobutylene.

17. The method of claim 16, wherein the pressure sensitive adhesive comprises sucrose acetate isobutyrate.

18. The method of claim 1, wherein the transdermal delivery system is sterile.

19. A transdermal delivery system comprising:
a backing layer, and
a reservoir laminated to the backing layer that comprises bupivacaine; and
wherein the reservoir is adapted to transdermally deliver the bupivacaine from the transdermal delivery system to a subject for a period such that the following mean plasma concentrations are achieved:

a mean plasma concentration, normalized to an initial loading of the transdermal delivery system, ranging from about 0.0003 to about 0.7 cm2/L at about 12 hours after initiation of the transdermal delivery; and a mean plasma concentration, normalized to an initial loading of the transdermal delivery system, ranging from about 0.0014 to about 0.4 cm2/L at about 24 hours after initiation of the transdermal delivery.

20. The transdermal delivery system of claim 19, wherein the reservoir is further adapted to transdermally deliver the bupivacaine from the transdermal delivery system to a subject for a three day period such that the following mean plasma concentrations are achieved: a mean plasma concentration, normalized to an initial loading of the transdermal delivery system, ranging from about 0.0013 to 0.3 cm²/L at about 48 hours after initiation of the transdermal delivery.

21. The transdermal delivery system of claim 19, wherein the reservoir is further adapted to transdermally deliver the bupivacaine from the transdermal delivery system to a subject for a three day period such that the following mean plasma concentrations are achieved: a mean plasma concentration, normalized to an initial loading of the transdermal delivery system, ranging from about 0.001 to 0.31 cm²/L at about 72 hours after initiation of the transdermal delivery.

22. The transdermal delivery system of claim 19, wherein the reservoir is further adapted to transdermally deliver the bupivacaine from the transdermal delivery system to a subject for a period such that the following mean plasma concentrations are achieved:

a mean plasma concentration, normalized to an initial loading of the transdermal delivery system, ranging from about 0.003 to about 0.07 cm²/L at about 12 hours after initiation of the transdermal delivery; and a mean plasma concentration, normalized to an initial loading of the transdermal delivery system, ranging from about 0.014 to about 0.04 cm²/L at about 24 hours after initiation of the transdermal delivery.

23. The transdermal delivery system of claim 22, wherein the reservoir is further adapted to transdermally deliver the bupivacaine from the transdermal delivery system to a subject for the period such that the following mean plasma concentrations are achieved: a mean plasma concentration, normalized to an initial loading of the transdermal delivery system, ranging from about 0.013 to 0.03 cm²/L at about 48 hours after initiation of the transdermal delivery.

24. The transdermal delivery system of claim 22, wherein the reservoir is further adapted to transdermally deliver the bupivacaine from the transdermal delivery system to a subject for the period such that the following mean plasma concentrations are achieved: a mean plasma concentration, normalized to an initial loading of the transdermal delivery system, ranging from about 0.01 to 0.031 cm²/L at about 72 hours after initiation of the transdermal delivery.

25. The transdermal delivery system of claim 19, wherein the period is about two days.

26. The transdermal delivery system of claim 19, wherein the reservoir is further adapted to provide a residual amount of bupivacaine in the transdermal delivery system following the two day period of use ranging from about 20 wt % to about 85 wt %, based on the total weight of bupivacaine in the transdermal delivery system prior to transdermal delivery.

27. The transdermal delivery system of claim 26, wherein the reservoir is further adapted to provide a residual amount of bupivacaine in the transdermal delivery system following the two day period of use ranging from about 30 wt % to about 75 wt % based on the total weight of bupivacaine in the transdermal delivery system prior to transdermal delivery.

28. The transdermal delivery system of claim 27, wherein the reservoir is further adapted to provide a residual amount of bupivacaine in the transdermal delivery system following the two day period of use ranging from about 40 wt % to about 60 wt % based on the total weight of bupivacaine in the transdermal delivery system prior to transdermal delivery.

29. The transdermal delivery system of claim 19, wherein the period is about 3 days.

30. The transdermal delivery system of claim 29, wherein the reservoir is further adapted to provide a residual amount of bupivacaine in the transdermal delivery system following the three day period of use ranging from about 20 wt % to about 85 wt %, based on the total weight of bupivacaine in the transdermal delivery system prior to transdermal delivery.

31. The transdermal delivery system of claim 30, wherein the reservoir is further adapted to provide a residual amount of bupivacaine in the transdermal delivery system following the three day period of use ranging from about 30 wt % to about 75 wt % based on the total weight of bupivacaine in the transdermal delivery system prior to transdermal delivery.

32. The transdermal delivery system of claim 31, wherein the reservoir is further adapted to provide a residual amount of bupivacaine in the transdermal delivery system following the three day period of use ranging from about 40 wt % to about 60 wt % based on the total weight of bupivacaine in the transdermal delivery system prior to transdermal delivery.

33. The transdermal delivery system of claim 19, wherein the transdermal delivery system comprises a pressure sensitive adhesive.

34. The transdermal delivery system of claim 33, wherein the pressure sensitive adhesive comprises polyisobutylene.

35. The transdermal delivery system of claim 34, wherein the pressure sensitive adhesive comprises sucrose acetate isobutyrate.

36. The transdermal delivery system of claim 19, wherein the transdermal delivery system is sterile.

37. A method comprising:
applying to a subject a transdermal delivery system that comprises bupivacaine;
transdermally delivering the bupivacaine from the transdermal delivery system to the subject for a three day period at one or more transdermal delivery rates such that the following relationships, normalized to an initial loading of the transdermal delivery system, are satisfied during the three day period:

$$0.003 \le C\text{max} \le 0.76 \text{ cm}^2/\text{L, and}$$

$$0.124 \le \text{AUC} \le 11.2 \text{ cm}^2*\text{hr/L}.$$

38. The method of claim 37, wherein the following relationship is satisfied during the three day period: $0.03 \le C\text{max} \le 0.76 \text{ cm}^2/\text{L}$.

39. The method of claim 37, wherein the following relationship is satisfied during the three day period: $1.2 \le \text{AUC} \le 7.0 \text{ cm}^2*\text{hr/L}$.

40. The method of claim 37, wherein the transdermal delivery system comprises a pressure sensitive adhesive.

41. The method of claim 40, wherein the pressure sensitive adhesive comprises polyisobutylene.

42. The method of claim 40 wherein the pressure sensitive adhesive comprises sucrose acetate isobutyrate.

43. The method of claim 37, wherein the transdermal delivery system is sterile.

44. A transdermal delivery system comprising:
a backing layer, and
a reservoir laminated to the backing layer that comprises bupivacaine; and
wherein the reservoir is adapted to transdermally deliver the bupivacaine from the transdermal delivery system to a subject for a three day period such that the following relationships are satisfied during the three day period:

$$0.003 \le C\text{max} \le 0.76 \text{ cm}^2/\text{L, and}$$

$$0.124 \le \text{AUC} \le 11.2 \text{ cm}^2*\text{hr/L}.$$

45. The transdermal delivery system of claim 44, wherein the reservoir is further adapted to satisfy the following relationship during the three day period:

$$0.03 \le C\text{max} \le 0.76 \text{ cm}^2/\text{L}.$$

46. The transdermal delivery system of claim 44, wherein the reservoir is further adapted to satisfy the following relationship during the three day period:

$$1.2 \le \text{AUC} \le 7.0 \text{ cm}^2*\text{hr/L}.$$

47. The transdermal delivery system of claim 44, wherein the transdermal delivery system comprises a pressure sensitive adhesive.

48. The transdermal delivery system of claim 47, wherein the pressure sensitive adhesive comprises polyisobutylene.

49. The transdermal delivery system of claim 47, wherein the pressure sensitive adhesive comprises sucrose acetate isobutyrate.

50. The transdermal delivery system of claim 44, wherein the transdermal delivery system is sterile.

51. A method comprising:
applying to a subject a transdermal delivery system that comprises bupivacaine;
transdermally delivering the bupivacaine from the transdermal delivery system to the subject for a period such that the following mean in vivo bupivacaine fluxes are achieved:
a mean in vivo bupivacaine flux from about 0.1 to about 8 microgram/cm2/hr at about 12 hours after initiation of the transdermal delivery; and
a mean in vivo bupivacaine flux from about 0.5 to about 6 microgram/cm2/hr at about 24 hours after initiation of the transdermal delivery.

52. The method of claim 51, wherein the following mean in vivo bupivacaine flux is further achieved: a mean in vivo bupivacaine flux from about 0.5 to about 6 microgram/cm$^2$/hr at about 48 hours after initiation of the transdermal delivery.

53. The method of claim 51, wherein the following mean in vivo bupivacaine flux is further achieved: a mean in vivo bupivacaine flux from about 0.5 to about 4 microgram/cm$^2$/hr at about 72 hours after initiation of the transdermal delivery.

54. The method of claim 51, wherein the transdermal delivery system comprises a pressure sensitive adhesive.

55. The method of claim 54, wherein the pressure sensitive adhesive comprises polyisobutylene.

56. The method of claim 54, wherein the pressure sensitive adhesive comprises sucrose acetate isobutyrate.

57. The method of claim 51, wherein the transdermal delivery system is sterile.

58. A method comprising:
applying to a subject a transdermal delivery system that comprises bupivacaine;

transdermally delivering the bupivacaine from the transdermal delivery system to the subject such that the mean in vivo bupivacaine fluxes at any time from about 12 hours after initiation of the transdermal delivery to about 48 hours after initiation of the transdermal delivery range from about 0.01 to about 25 microgram/cm2/hr.

59. A method comprising:
applying to a subject a transdermal delivery system that comprises bupivacaine;
transdermally delivering the bupivacaine from the transdermal delivery system to the subject such that the mean in vivo bupivacaine fluxes at any time from about 12 hours after initiation of the transdermal delivery to about 72 hours after initiation of the transdermal delivery range from about 0.01 to about 25 microgram/cm2/hr.

60. A transdermal delivery system comprising:
a backing layer, and
a reservoir laminated to the backing layer that comprises bupivacaine; and
wherein the reservoir is adapted to transdermally deliver the bupivacaine from the transdermal delivery system to a subject for a three day period such that the following mean in vivo bupivacaine fluxes are achieved:
a mean in vivo bupivacaine flux from about 0.1 to about 8 microgram/cm2/hr at about 12 hours after initiation of the transdermal delivery; and
a mean in vivo bupivacaine flux from about 0.5 to about 6 microgram/cm2/hr at about 24 hours after initiation of the transdermal delivery.

61. The transdermal delivery system of claim 60, wherein the reservoir is further adapted to provide the following: a mean in vivo bupivacaine flux from about 0.5 to about 6 microgram/cm$^2$/hr at about 48 hours after initiation of the transdermal delivery.

62. The transdermal delivery system of claim 60, wherein the reservoir is further adapted to provide the following: a mean in vivo bupivacaine flux from about 0.5 to about 4 microgram/cm$^2$/hr at about 72 hours after initiation of the transdermal delivery.

63. The transdermal delivery system of claim 60, wherein the transdermal delivery system comprises a pressure sensitive adhesive.

64. The transdermal delivery system of claim 63, wherein the pressure sensitive adhesive comprises polyisobutylene.

65. The transdermal delivery system of claim 63, wherein the pressure sensitive adhesive comprises sucrose acetate isobutyrate.

66. The transdermal delivery system of claim 60, wherein the transdermal delivery system is sterile.

67. A method comprising:
applying to a transdermal delivery system that comprises bupivacaine;
transdermally delivering the bupivacaine from the transdermal delivery system such that the following mean in vitro bupivacaine fluxes are achieved:
a mean in vitro bupivacaine flux ranging from about 0.1 to about 8 microgram/cm2/hr at about 12 hours after initiation of the transdermal delivery; and
a mean in vitro bupivacaine flux ranging from about 0.25 to about 6 microgram/cm2/hr at about 24 hours after initiation of the transdermal delivery.

68. The method of claim 67, wherein the following mean in vitro bupivacaine flux is further achieved: a mean in vitro bupivacaine flux ranging from about 0.25 to about 6 microgram/cm$^2$/hr at about 48 hours after initiation of the transdermal delivery.

69. The method of claim 67, wherein the following mean in vitro bupivacaine flux is further achieved: a mean in vitro bupivacaine flux ranging from about 0.25 to about 5 microgram/cm$^2$/hr at about 72 hours after initiation of the transdermal delivery.

70. The method of claim 67, wherein the transdermal delivery system comprises a pressure sensitive adhesive.

71. The method of claim 70, wherein the pressure sensitive adhesive comprises polyisobutylene.

72. The method of claim 70, wherein the pressure sensitive adhesive comprises sucrose acetate isobutyrate.

73. The method of claim 67, wherein the transdermal delivery system is sterile.

74. A method comprising:
applying a transdermal delivery system that comprises bupivacaine;
transdermally delivering the bupivacaine from the transdermal delivery system such that a mean in vitro bupivacaine flux at any time from about 12 hours after initiation of the transdermal delivery to about 48 hours after initiation of the transdermal delivery ranges from about 0.01 to about 25 microgram/cm2/hr.

75. A method comprising:
applying a transdermal delivery system that comprises bupivacaine;
transdermally delivering the bupivacaine from the transdermal delivery system such that a mean in vitro bupivacaine flux at any time from about 12 hours after initiation of the transdermal delivery to about 72 hours after initiation of the transdermal delivery ranges from about 0.01 to about 25 microgram/cm2/hr.

76. A transdermal delivery system comprising:
a backing layer, and
a reservoir laminated to the backing layer that comprises bupivacaine; and
wherein the reservoir is adapted to transdermally deliver the bupivacaine from the transdermal delivery system to a subject for a three day period such that the following mean in vitro bupivacaine fluxes are achieved:
a mean in vitro bupivacaine flux from about 0.1 to about 8 microgram/cm2/hr at about 12 hours after initiation of the transdermal delivery; and
a mean in vitro bupivacaine flux from about 0.5 to about 6 microgram/cm2/hr at about 24 hours after initiation of the transdermal delivery.

77. The transdermal delivery system of claim 76, wherein the reservoir is further adapted to provide the following: a mean in vitro bupivacaine flux from about 0.5 to about 6 microgram/cm$^2$/hr at about 48 hours after initiation of the transdermal delivery.

78. The transdermal delivery system of claim 76, wherein the reservoir is further adapted to provide the following: a mean in vitro bupivacaine flux from about 0.5 to about 4 microgram/cm$^2$/hr at about 72 hours after initiation of the transdermal delivery.

79. The transdermal delivery system of claim 76, wherein the transdermal delivery system comprises a pressure sensitive adhesive.

80. The transdermal delivery system of claim 79, wherein the pressure sensitive adhesive comprises polyisobutylene.

81. The transdermal delivery system of claim 79, wherein the pressure sensitive adhesive comprises sucrose acetate isobutyrate.

82. The transdermal delivery system of claim 76, wherein the transdermal delivery system is sterile.

83. A transdermal delivery system comprising:
a backing layer, and
a reservoir comprising a pressure sensitive adhesive composition laminated to the backing layer;
wherein the pressure sensitive adhesive composition comprises one or more rheology and surface energy modifying agents present in an amount effective to reduce a peel force of the transdermal delivery system by at least 10% compared to the peel force of the transdermal delivery system comprising the pressure sensitive adhesive composition that does not comprise the one or more rheology and surface energy modifying agents.

84. The transdermal delivery system of claim 83, wherein the one or more rheology and surface energy modifying agents comprises sucrose acetate isobutyrate, 1,6-hexanediol lactate glycolate, 1,6-hexanediol lactate caproate, glycerol lactate caproate, glycerol lactate glycolate, glycerol lactate glycolate with succinic anhydride, glycolic acid lactate glycolate, or lactic acid lactate glycolate.

85. The transdermal delivery system of claim 83, wherein the one or more rheology and surface energy modifying agents comprises sucrose acetate isobutyrate.

86. The transdermal delivery system of claim 83, present in an amount effective to reduce a peel force of the transdermal delivery system by at least 20% compared to the peel force of the transdermal delivery system comprising the pressure sensitive adhesive composition that does not comprise the one or more rheology and surface energy modifying agents.

87. The transdermal delivery system of claim 86, wherein present in an amount effective to reduce a peel force of the transdermal delivery system by at least 30% compared to the peel force of the transdermal delivery system comprising the pressure sensitive adhesive composition that does not comprise the one or more rheology and surface energy modifying agents.

88. The transdermal delivery system of claim 83, wherein the pressure sensitive adhesive comprises polyisobutylene.

89. The transdermal delivery system of claim 83, further comprising a release liner.

90. The transdermal delivery system of claim 83, wherein the pressure sensitive adhesive comprises bupivacaine.

91. A transdermal delivery system comprising:
a backing layer, and
a reservoir comprising a pressure sensitive adhesive composition laminated to the backing layer;
wherein the pressure sensitive adhesive composition comprises from about 10 to about 30 wt. % of a polyisobutyrate having a viscosity average molecular weight of about 1,100,000, from about 5 to about 40 wt. % of a polyisobutyrate having a viscosity average molecular weight of about 50,000, from about 30 to about 70 wt. % of polybutene, from about 0.1 to about 10 wt. % of sucrose acetate isobutyrate, and from about 1 to about 10 wt. % of bupivacaine, where the weight % is based on the total weight of the pressure sensitive adhesive composition in a dry state.

92. The transdermal delivery system of claim 91, wherein the pressure sensitive adhesive composition comprises from about 15 to about 20 wt. % of a polyisobutyrate having a viscosity average molecular weight of about 1,100,000, from about 15 to about 25 wt. % of a polyisobutyrate having a viscosity average molecular weight of about 50,000, from about 45 to about 65 wt. % of polybutene, from about 1 to about 7 wt. % of sucrose acetate isobutyrate, and from about 2 to about 7 wt. % of bupivacaine, where the weight % is based on the total weight of the pressure sensitive adhesive composition in a dry state.

93. The transdermal delivery system of claim 91, further comprising a release liner.

94. The transdermal delivery system of claim 91, wherein the backing layer comprises a monolithic material, a multi-layer material, a breathable material or an occlusive material.

95. The transdermal delivery system of claim 94, wherein the backing layer comprises woven or non-woven fabric.

96. The transdermal delivery system of claim 95, wherein the backing layer comprises a non-woven polyester fabric.

97. The transdermal delivery system of claim 91, wherein the pressure sensitive adhesive composition comprises metal oxides, inorganic salts, synthetic polymers, or clays.

98. The transdermal delivery system of claim 97, wherein the pressure sensitive adhesive composition comprises silicon dioxide; zinc oxide; magnesium oxide; titanium oxide; calcium oxide; calcium, magnesium or sodium carbonate; calcium or magnesium sulfate; calcium phosphate; methacrylic resin; nylon; polyethylene; talc; bentonite; or kaolin.

99. The transdermal delivery system of claim 91, wherein the pressure sensitive adhesive composition comprises aliphatic hydrocarbons; aromatic hydrocarbons; hydrogenated esters; polyterpenes; silica, hydrogenated wood resins; tackifying resins, aliphatic hydrocarbon resins made from cationic polymerization of petrochemical feedstocks or thermal polymerization and subsequent hydrogenation of petrochemical feedstocks, rosin ester tackifiers, mineral oil, polybutyl-methacrylate, high molecular weight acrylates, or combinations of the above.

100. The transdermal delivery system of claim 91, wherein the reservoir possesses a thickness ranging from about 1 to about 10 mils.

101. A transdermal delivery system comprising:
a backing layer, and
a reservoir laminated to the backing layer that comprises bupivacaine;
wherein the reservoir is adapted to transdermally deliver the bupivacaine from the transdermal delivery system to a subject for a three day period; and
wherein the transdermal delivery system is sterile.

102. The transdermal delivery system of claim 101, wherein the transdermal delivery system comprises a pressure sensitive adhesive.

103. The transdermal delivery system of claim 102, wherein the pressure sensitive adhesive comprises polyisobutylene.

104. The transdermal delivery system of claim 102 wherein the pressure sensitive adhesive comprises sucrose acetate isobutyrate.

105. The transdermal delivery system of claim 101, wherein the reservoir possesses a thickness ranging from about 1 to about 10 mils.

106. The transdermal delivery system of claim 101, wherein the backing layer comprises woven or non-woven fabric.

107. A method comprising:
applying to a transdermal delivery system that comprises bupivacaine;
transdermally delivering the bupivacaine from the transdermal delivery system for a two day period,
wherein a residual amount of bupivacaine in the transdermal delivery system following the two day period of use ranges from about 20 wt % to about 85 wt %, based on the total weight of bupivacaine in the transdermal delivery system prior to transdermal delivery.

108. The method of claim 107, wherein a residual amount of bupivacaine in the transdermal delivery system following the two day period of use ranges from about 30 wt % to about 75 wt % based on the total weight of bupivacaine in the transdermal delivery system prior to transdermal delivery.

109. The method of claim 108, wherein a residual amount of bupivacaine in the transdermal delivery system following the two day period of use ranges from about 40 wt % to about 60 wt % based on the total weight of bupivacaine in the transdermal delivery system prior to transdermal delivery.

110. A method comprising:
applying to a transdermal delivery system that comprises bupivacaine;
transdermally delivering the bupivacaine from the transdermal delivery system for a three day period,
wherein a residual amount of bupivacaine in the transdermal delivery system following the two day period of use ranges from about 20 wt % to about 85 wt %, based on the total weight of bupivacaine in the transdermal delivery system prior to transdermal delivery.

111. The method of claim 110, wherein a residual amount of bupivacaine in the transdermal delivery system following the three day period of use ranges from about 30 wt % to about 75 wt % based on the total weight of bupivacaine in the transdermal delivery system prior to transdermal delivery.

112. The method of claim 111, wherein a residual amount of bupivacaine in the transdermal delivery system following the three day period of use ranges from about 40 wt % to about 60 wt % based on the total weight of bupivacaine in the transdermal delivery system prior to transdermal delivery.

113. A method comprising:
applying to a subject a transdermal delivery system that comprises bupivacaine;
transdermally delivering the bupivacaine from the transdermal delivery system for a period to the subject such that the following mean plasma concentrations are achieved:
a mean plasma concentration, normalized to an initial loading of the transdermal delivery system, ranging from about 0.0003 to about 0.7 cm2/L at about 12 hours after initiation of the transdermal delivery.

114. The method of claim 113, wherein the following mean plasma concentration are achieved:
a mean plasma concentration, normalized to an initial loading of the transdermal delivery system, ranging from about 0.0014 to about 0.4 cm2/L at about 24 hours after initiation of the transdermal delivery.

115. The method of claim 113, wherein the following mean plasma concentration is further achieved: a mean plasma concentration, normalized to an initial loading of the transdermal delivery system, ranging from about 0.0013 to 0.3 cm2/L at about 48 hours after initiation of the transdermal delivery.

116. The method of claim 113, wherein the following mean plasma concentration is further achieved: a mean plasma concentration, normalized to an initial loading of the transdermal delivery system, ranging from about 0.001 to 0.31 cm2/L at about 72 hours after initiation of the transdermal delivery.

117. The method of claim 113, wherein the following mean plasma concentration are achieved:
a mean plasma concentration, normalized to an initial loading of the transdermal delivery system, ranging from about 0.003 to about 0.07 cm2/L at about 12 hours after initiation of the transdermal delivery.

118. The method of claim 113, wherein the following mean plasma concentration are achieved:
a mean plasma concentration, normalized to an initial loading of the transdermal delivery system, ranging from about 0.014 to about 0.04 cm2/L at about 24 hours after initiation of the transdermal delivery.

119. The method of claim 118, wherein the following mean plasma concentration is further achieved: a mean plasma concentration, normalized to an initial loading of the transdermal delivery system, ranging from about 0.013 to 0.03 cm2/L at about 48 hours after initiation of the transdermal delivery.

120. The method of claim 118, wherein the following mean plasma concentration is further achieved: a mean plasma concentration, normalized to an initial loading of the transdermal delivery system, ranging from about 0.01 to 0.031 cm2/L at about 72 hours after initiation of the transdermal delivery.

121. The method of claim 113, wherein the period is about two days.

122. The method of claim 121, wherein a residual amount of bupivacaine in the transdermal delivery system following the two day period of use ranges from about 20 wt % to about 85 wt %, based on the total weight of bupivacaine in the transdermal delivery system prior to transdermal delivery.

123. The method of claim 121, wherein a residual amount of bupivacaine in the transdermal delivery system following the two day period of use ranges from about 30 wt % to about 75 wt % based on the total weight of bupivacaine in the transdermal delivery system prior to transdermal delivery.

124. The method of claim 123, wherein a residual amount of bupivacaine in the transdermal delivery system following the two day period of use ranges from about 40 wt % to about 60 wt % based on the total weight of bupivacaine in the transdermal delivery system prior to transdermal delivery.

125. The method of claim 113, wherein the period is about three days.

126. The method of claim 125, wherein a residual amount of bupivacaine in the transdermal delivery system following the three day period of use ranges from about 20 wt % to about 85 wt %, based on the total weight of bupivacaine in the transdermal delivery system prior to transdermal delivery.

127. The method of claim 126, wherein a residual amount of bupivacaine in the transdermal delivery system following the three day period of use ranges from about 30 wt % to about 75 wt % based on the total weight of bupivacaine in the transdermal delivery system prior to transdermal delivery.

128. The method of claim 127, wherein a residual amount of bupivacaine in the transdermal delivery system following the three day period of use ranges from about 40 wt % to about 60 wt % based on the total weight of bupivacaine in the transdermal delivery system prior to transdermal delivery.

129. The method of claim 113, wherein the transdermal delivery system comprises a pressure sensitive adhesive.

130. The method of claim 129, wherein the pressure sensitive adhesive comprises polyisobutylene.

131. The method of claim 130, wherein the pressure sensitive adhesive comprises sucrose acetate isobutyrate.

132. The method of claim 113, wherein the transdermal delivery system is sterile.

133. A transdermal delivery system comprising:
a backing layer, and
a reservoir laminated to the backing layer that comprises bupivacaine; and
wherein the reservoir is adapted to transdermally deliver the bupivacaine from the transdermal delivery system to a subject for a period such that the following mean plasma concentrations are achieved:
a mean plasma concentration, normalized to an initial loading of the transdermal delivery system, ranging from about 0.0003 to about 0.7 cm2/L at about 12 hours after initiation of the transdermal delivery.

134. The transdermal delivery system of claim 133, wherein the reservoir is further adapted to transdermally deliver the bupivacaine from the transdermal delivery system to a subject for a period such that the following mean plasma concentrations are achieved: a mean plasma concentration, normalized to an initial loading of the transdermal delivery system, ranging from about 0.0014 to about 0.4 cm2/L at about 24 hours after initiation of the transdermal delivery.

135. The transdermal delivery system of claim 133, wherein the reservoir is further adapted to transdermally deliver the bupivacaine from the transdermal delivery system to a subject for a period such that the following mean plasma concentrations are achieved: a mean plasma concentration, normalized to an initial loading of the transdermal delivery system, ranging from about 0.0013 to 0.3 cm2/L at about 48 hours after initiation of the transdermal delivery.

136. The transdermal delivery system of claim 133, wherein the reservoir is further adapted to transdermally deliver the bupivacaine from the transdermal delivery system to a subject for a period such that the following mean plasma concentrations are achieved: a mean plasma concentration, normalized to an initial loading of the transdermal delivery system, ranging from about 0.001 to 0.31 cm2/L at about 72 hours after initiation of the transdermal delivery.

137. The transdermal delivery system of claim 133, wherein the reservoir is further adapted to transdermally deliver the bupivacaine from the transdermal delivery system to a subject for a period such that the following mean plasma concentrations are achieved:

a mean plasma concentration, normalized to an initial loading of the transdermal delivery system, ranging from about 0.003 to about 0.07 cm2/L at about 12 hours after initiation of the transdermal delivery.

138. The transdermal delivery system of claim 137, wherein the reservoir is further adapted to transdermally deliver the bupivacaine from the transdermal delivery system to a subject for a period such that the following mean plasma concentrations are achieved: a mean plasma concentration, normalized to an initial loading of the transdermal delivery system, ranging from about 0.014 to about 0.04 cm2/L at about 24 hours after initiation of the transdermal delivery.

139. The transdermal delivery system of claim 138, wherein the reservoir is further adapted to transdermally deliver the bupivacaine from the transdermal delivery system to a subject for the period such that the following mean plasma concentrations are achieved: a mean plasma concentration, normalized to an initial loading of the transdermal delivery system, ranging from about 0.013 to 0.03 cm2/L at about 48 hours after initiation of the transdermal delivery.

140. The transdermal delivery system of claim 138, wherein the reservoir is further adapted to transdermally deliver the bupivacaine from the transdermal delivery system to a subject for the period such that the following mean plasma concentrations are achieved: a mean plasma concentration, normalized to an initial loading of the transdermal delivery system, ranging from about 0.01 to 0.031 cm2/L at about 72 hours after initiation of the transdermal delivery.

141. The transdermal delivery system of claim 133, wherein the period is about two days.

142. The transdermal delivery system of claim 141, wherein the reservoir is further adapted to provide a residual amount of bupivacaine in the transdermal delivery system following the two day period of use ranging from about 20 wt % to about 85 wt %, based on the total weight of bupivacaine in the transdermal delivery system prior to transdermal delivery.

143. The transdermal delivery system of claim 142, wherein the reservoir is further adapted to provide a residual amount of bupivacaine in the transdermal delivery system following the two day period of use ranging from about 30 wt % to about 75 wt % based on the total weight of bupivacaine in the transdermal delivery system prior to transdermal delivery.

144. The transdermal delivery system of claim 143, wherein the reservoir is further adapted to provide a residual amount of bupivacaine in the transdermal delivery system following the two day period of use ranging from about 40 wt % to about 60 wt % based on the total weight of bupivacaine in the transdermal delivery system prior to transdermal delivery.

145. The transdermal delivery system of claim 133, wherein the period is about 3 days.

146. The transdermal delivery system of claim 145, wherein the reservoir is further adapted to provide a residual amount of bupivacaine in the transdermal delivery system following the three day period of use ranging from about 20 wt % to about 85 wt %, based on the total weight of bupivacaine in the transdermal delivery system prior to transdermal delivery.

147. The transdermal delivery system of claim 146, wherein the reservoir is further adapted to provide a residual amount of bupivacaine in the transdermal delivery system following the three day period of use ranging from about 30 wt % to about 75 wt % based on the total weight of bupivacaine in the transdermal delivery system prior to transdermal delivery.

148. The transdermal delivery system of claim 147, wherein the reservoir is further adapted to provide a residual amount of bupivacaine in the transdermal delivery system following the three day period of use ranging from about 40 wt % to about 60 wt % based on the total weight of bupivacaine in the transdermal delivery system prior to transdermal delivery.

149. The transdermal delivery system of claim 133, wherein the transdermal delivery system comprises a pressure sensitive adhesive.

150. The transdermal delivery system of claim 149, wherein the pressure sensitive adhesive comprises polyisobutylene.

151. The transdermal delivery system of claim 150, wherein the pressure sensitive adhesive comprises sucrose acetate isobutyrate.

152. The transdermal delivery system of claim 133, wherein the transdermal delivery system is sterile.

What is claimed is:
1. A system comprising:
a backing layer;
a reservoir; and
a release liner;
wherein the reservoir is an adhesive type matrix comprising a blend of:
(i) a high molecular weight polyisobutylene having a viscosity average molecular weight of 450,000 to 2,100,000; and
(ii) a low molecular weight polyisobutylene having a viscosity average molecular weight of 1,000 to 450,000; and
the reservoir further comprising sucrose acetate isobutyrate in an amount effective to reduce a peel force of the system; and
the reservoir further comprising bupivacaine.

2. The system of claim 1, wherein the ratio of high molecular weight polyisobutylene:low molecular weight polyisobutylene is from 20:80 to 70:30 by weight.

3. The system of claim 2, wherein the ratio of high molecular weight polyisobutylene:low molecular weight polyisobutylene is from 40:60 to 50:50 by weight.

4. The system of claim 1, wherein the high molecular weight polyisobutylene has a viscosity average molecular weight of about 1,100,000 and the low molecular weight polyisobutylene has a viscosity average molecular weight of about 50,000-55,000.

5. The system of claim 1, wherein the reservoir further comprises a plasticizer.

6. The system of claim 5, wherein the plasticizer is selected from polybutene, mineral oil, linseed oil, octyl palmitate, squalene, silicone oil, isobutyl stearate, olive oil, isopropyl myristate, isostearyl alcohol and oleyl alcohol.

7. The system of claim 6, wherein said plasticizer comprises polybutene.

8. The system of claim 1, wherein the backing layer comprises a breathable material comprising woven or non-woven fabric.

9. The system of claim 1, wherein the backing layer comprises a non-woven polyester fabric.

10. The system of claim 1, wherein the bupivacaine comprises bupivacaine free base.

11. The system of claim 1, wherein the reservoir has a thickness of from 1 to 10 mils.

12. The system of claim 1, wherein the reservoir does not comprise a permeation enhancer.

13. The system of claim 1, wherein the system does not comprise a rate controlling membrane.

14. A method of treating pain, comprising applying the system of claim 10 to a subject in need thereof.

15. A method comprising:
applying to a subject the system of claim 10, wherein the bupivacaine is transdermally delivered from the system to the subject for a period such that the following mean in vivo bupivacaine fluxes are achieved:
a mean in vivo bupivacaine flux from about 0.1 to about 8 microgram/cm$^2$/hr at about 12 hours after initiation of the transdermal delivery; and
a mean in vivo bupivacaine flux from about 0.5 to about 6 microgram/cm$^2$/hr at about 24 hours after initiation of the transdermal delivery.

16. A method comprising:
applying to a subject the system of claim 10, wherein the bupivacaine is transdermally delivered from the system to the subject such that the mean in vivo bupivacaine fluxes at any time from about 12 hours after initiation of the transdermal delivery to about 48 hours after initiation of the transdermal delivery range from about 0.01 to about 25 microgram/cm$^2$/hr.

17. A system comprising:
a backing layer;
a reservoir; and
a release liner;
wherein the reservoir is an adhesive type matrix comprising a blend of:
(i) a high molecular weight polyisobutylene having a viscosity average molecular weight of 450,000 to 2,100,000; and
(ii) a low molecular weight polyisobutylene having a viscosity average molecular weight of 1,000 to 450,000; and
the reservoir further comprising at least one member selected from 1,6-hexanediol lactate glycolate, 1,6-hexanediol lactate caproate, glycerol lactate caproate, glycerol lactate glycolate, glycerol lactate glycolate with succinic anhydride, glycolic acid lactate glycolate, and lactic acid lactate glycolate; and
the reservoir further comprising bupivacaine.

18. The system of claim 17, wherein the ratio of high molecular weight polyisobutylene:low molecular weight polyisobutylene is from 20:80 to 70:30 by weight.

19. The system of claim 18, wherein the ratio of high molecular weight polyisobutylene:low molecular weight polyisobutylene is from 40:60 to 50:50 by weight.

20. The system of claim 17, wherein the high molecular weight polyisobutylene has a viscosity average molecular weight of about 1,100,000 and the low molecular weight polyisobutylene has a viscosity average molecular weight of about 50,000-55,000.

21. The system of claim 17, wherein the reservoir further comprises a plasticizer.

22. The system of claim 21, wherein the plasticizer is selected from polybutene, mineral oil, linseed oil, octyl palmitate, squalene, silicone oil, isobutyl stearate, olive oil, isopropyl myristate, isostearyl alcohol and oleyl alcohol.

23. The system of claim 22, wherein said plasticizer comprises polybutene.

24. The system of claim 17, wherein the backing layer comprises a breathable material comprising woven or non-woven fabric.

25. The system of claim 17, wherein the backing layer comprises a non-woven polyester fabric.

26. The system of claim 17, wherein the bupivacaine comprises bupivacaine free base.

27. The system of claim 17, wherein the reservoir has a thickness of from 1 to 10 mils.

28. The system of claim 17, wherein the reservoir does not comprise a permeation enhancer.

29. The system of claim 17, wherein the system does not comprise a rate controlling membrane.

30. A method of treating pain, comprising applying the system of claim 26 to a subject in need thereof.

31. A method comprising:
applying to a subject the system of claim 26, wherein the bupivacaine is transdermally delivered from the system to the subject for a period such that the following mean in vivo bupivacaine fluxes are achieved:
a mean in vivo bupivacaine flux from about 0.1 to about 8 microgram/cm$^2$/hr at about 12 hours after initiation of the transdermal delivery; and
a mean in vivo bupivacaine flux from about 0.5 to about 6 microgram/cm$^2$/hr at about 24 hours after initiation of the transdermal delivery.

32. A method comprising:
applying to a subject the system of claim 26, wherein the bupivacaine is transdermally delivered from the system to the subject such that the mean in vivo bupivacaine fluxes at any time from about 12 hours after initiation of the transdermal delivery to about 48 hours after initiation of the transdermal delivery range from about 0.01 to about 25 microgram/cm$^2$/hr.

* * * * *

UNITED STATES PATENT AND TRADEMARK OFFICE
CERTIFICATE OF CORRECTION

PATENT NO.       : 8,956,644 B2
APPLICATION NO.  : 13/679685
DATED            : February 17, 2015
INVENTOR(S)      : Su Il Yum et al.

It is certified that error appears in the above-identified patent and that said Letters Patent is hereby corrected as shown below:

On the title page item (72), replace "Su II Yum" with "Su Il Yum".

Signed and Sealed this
First Day of March, 2016

Michelle K. Lee
*Director of the United States Patent and Trademark Office*